(12) United States Patent
Stahmann et al.

(10) Patent No.: US 11,439,304 B2
(45) Date of Patent: Sep. 13, 2022

(54) SYSTEMS AND METHODS INCLUDING ELECTROLYTE SENSOR FUSION

(71) Applicant: Cardiac Pacemakers, Inc., St. Paul, MN (US)

(72) Inventors: Jeffrey E. Stahmann, Ramsey, MN (US); Yingbo Li, Shanghai (CN); Michael John Kane, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 160 days.

(21) Appl. No.: 16/038,737

(22) Filed: Jul. 18, 2018

(65) Prior Publication Data
US 2019/0046032 A1 Feb. 14, 2019

(30) Foreign Application Priority Data
Aug. 10, 2017 (CN) .......................... 201710681567.3

(51) Int. Cl.
A61B 5/1455 (2006.01)
A61B 5/00 (2006.01)
(Continued)

(52) U.S. Cl.
CPC .......... *A61B 5/0006* (2013.01); *A61B 5/1473* (2013.01); *A61B 5/14546* (2013.01); *A61B 5/283* (2021.01); *A61B 5/333* (2021.01); *A61B 5/686* (2013.01); *G01N 27/3273* (2013.01); *A61B 5/0031* (2013.01); *A61B 5/14532* (2013.01); *A61B 5/14539* (2013.01);
(Continued)

(58) Field of Classification Search
None
See application file for complete search history.

(56) References Cited

U.S. PATENT DOCUMENTS 556,421 A 3/1896 Judge
4,200,110 A 4/1980 Peterson et al.
(Continued)

FOREIGN PATENT DOCUMENTS

EP 2967333 1/2016
EP 3440999 2/2019
(Continued)

OTHER PUBLICATIONS

Non-Final Office Action for U.S. Appl. No. 15/992,823 dated May 5, 2020 (51 pages).
(Continued)

Primary Examiner — Erica S Lee
(74) Attorney, Agent, or Firm — Pauly, DeVries Smith & Deffner LLC

(57) ABSTRACT

Embodiments herein relate to systems and methods for combining data from different types of sensors. In an embodiment, a medical system is included. The medical system can include a first sensor configured to produce a first value for an analyte and a second sensor different than the first sensor, the second sensor configured to produce a second value for the analyte. The medical system can also include a controller configured to receive the first and second values. The controller can create a blended analyte value from the first value and second value. Other embodiments are included herein.

16 Claims, 8 Drawing Sheets

(51) Int. Cl.
  *A61B 5/1473* (2006.01)
  *A61B 5/145* (2006.01)
  *G01N 27/327* (2006.01)
  *A61B 5/283* (2021.01)
  *A61B 5/333* (2021.01)
  *G01N 27/416* (2006.01)
  *G01N 27/413* (2006.01)

(52) U.S. Cl.
  CPC .......... *A61B 5/7278* (2013.01); *G01N 27/413* (2013.01); *G01N 27/4167* (2013.01)

(56) References Cited

U.S. PATENT DOCUMENTS

| | | | |
|---|---|---|---|
| 4,321,057 A | 3/1982 | Buckles | |
| 4,344,438 A | 8/1982 | Schultz et al. | |
| 4,399,099 A | 8/1983 | Buckles | |
| 4,680,268 A | 7/1987 | Clark | |
| 4,704,029 A | 11/1987 | Van Heuvelen | |
| 4,721,677 A | 1/1988 | Clark | |
| 4,750,494 A | 6/1988 | King | |
| 4,750,495 A | 6/1988 | Moore et al. | |
| 4,890,621 A | 1/1990 | Hakky | |
| 4,903,701 A | 2/1990 | Moore | |
| 4,981,779 A | 1/1991 | Wagner | |
| 5,001,054 A | 3/1991 | Wagner | |
| 5,040,533 A | 8/1991 | Fearnot | |
| 5,090,326 A | 2/1992 | Altenau et al. | |
| 5,209,231 A | 5/1993 | Cote et al. | |
| 5,267,151 A | 11/1993 | Ham et al. | |
| 5,275,171 A | 1/1994 | Barcel | |
| 5,312,439 A | 5/1994 | Loeb | |
| 5,312,454 A | 5/1994 | Roline et al. | |
| 5,330,718 A | 7/1994 | Hui et al. | |
| 5,333,609 A | 8/1994 | Bedingham et al. | |
| 5,342,406 A | 8/1994 | Thompson | |
| 5,342,789 A | 8/1994 | Chick et al. | |
| 5,355,880 A | 10/1994 | Thomas et al. | |
| 5,378,432 A | 1/1995 | Bankert et al. | |
| 5,419,329 A | 5/1995 | Smith et al. | |
| 5,457,535 A | 10/1995 | Schmidtke et al. | |
| 5,476,434 A | 12/1995 | Kalb et al. | |
| 5,553,616 A | 9/1996 | Ham et al. | |
| 5,556,421 A | 9/1996 | Prutchi et al. | |
| 5,560,356 A | 10/1996 | Peyman | |
| 5,605,152 A | 2/1997 | Slate et al. | |
| 5,607,644 A | 3/1997 | Olstein et al. | |
| 5,660,163 A | 8/1997 | Schulman et al. | |
| 5,728,281 A | 3/1998 | Holmstrom et al. | |
| 5,730,125 A | 3/1998 | Prutchi et al. | |
| 5,741,211 A * | 4/1998 | Renirie .............. | A61B 5/14532 600/300 |
| 5,797,898 A | 8/1998 | Santini et al. | |
| 5,830,138 A | 11/1998 | Wilson | |
| 5,833,603 A | 11/1998 | Kovacs et al. | |
| 5,854,078 A | 12/1998 | Asher | |
| 5,871,442 A | 2/1999 | Madarasz et al. | |
| 5,902,326 A | 5/1999 | Lessar et al. | |
| 5,958,782 A | 9/1999 | Bentsen et al. | |
| 5,995,860 A | 11/1999 | Sun et al. | |
| 6,002,954 A | 12/1999 | Van Antwerp et al. | |
| 6,011,984 A | 1/2000 | Van Antwerp et al. | |
| 6,040,194 A | 3/2000 | Chick et al. | |
| 6,049,727 A | 4/2000 | Crothall | |
| 6,070,093 A | 5/2000 | Oosta et al. | |
| 6,097,139 A | 8/2000 | Tuck et al. | |
| 6,122,536 A | 9/2000 | Sun et al. | |
| 6,123,861 A | 9/2000 | Santini et al. | |
| 6,125,290 A | 9/2000 | Miesel | |
| 6,125,291 A | 9/2000 | Miesel et al. | |
| 6,134,459 A | 10/2000 | Roberts et al. | |
| 6,144,866 A | 11/2000 | Miesel et al. | |
| 6,163,714 A | 12/2000 | Stanley et al. | |
| 6,175,642 B1 | 1/2001 | Gobbi et al. | |
| 6,187,599 B1 | 2/2001 | Asher et al. | |
| 6,216,022 B1 | 4/2001 | Tyrrell et al. | |
| 6,219,137 B1 | 4/2001 | Vo-Dinh | |
| 6,232,130 B1 | 5/2001 | Wolf | |
| 6,236,870 B1 | 5/2001 | Madarasz et al. | |
| 6,256,522 B1 | 7/2001 | Schultz | |
| 6,267,724 B1 | 7/2001 | Taylor et al. | |
| 6,268,161 B1 | 7/2001 | Han et al. | |
| 6,277,627 B1 | 8/2001 | Hellinga | |
| 6,304,766 B1 | 10/2001 | Colvin, Jr. | |
| 6,330,464 B1 | 12/2001 | Colvin et al. | |
| 6,343,223 B1 | 1/2002 | Chin et al. | |
| 6,344,340 B1 | 2/2002 | Dibner et al. | |
| 6,368,274 B1 | 4/2002 | Van Antwerp et al. | |
| 6,383,767 B1 | 5/2002 | Polak | |
| 6,438,397 B1 | 8/2002 | Bosquet et al. | |
| 6,442,409 B1 | 8/2002 | Peyman | |
| 6,454,710 B1 | 9/2002 | Ballerstadt et al. | |
| 6,466,821 B1 | 10/2002 | Pianca et al. | |
| 6,491,639 B1 | 12/2002 | Turcott | |
| 6,491,666 B1 | 12/2002 | Santini, Jr. et al. | |
| 6,505,059 B1 | 1/2003 | Kollias et al. | |
| 6,521,446 B2 | 2/2003 | Hellinga | |
| 6,527,762 B1 | 3/2003 | Santini, Jr. et al. | |
| 6,544,800 B2 | 4/2003 | Asher | |
| 6,551,838 B2 | 4/2003 | Santini, Jr. et al. | |
| 6,579,690 B1 | 6/2003 | Bonnecaze et al. | |
| 6,594,092 B2 | 7/2003 | Von Freyhold et al. | |
| 6,594,510 B2 | 7/2003 | Madarasz et al. | |
| 6,602,521 B1 | 8/2003 | Ting et al. | |
| 6,625,479 B1 | 9/2003 | Weber et al. | |
| 6,666,821 B2 | 12/2003 | Keimel et al. | |
| 6,671,527 B2 | 12/2003 | Petersson et al. | |
| 6,673,596 B1 | 1/2004 | Sayler et al. | |
| 6,682,938 B1 | 1/2004 | Satcher, Jr. et al. | |
| 6,694,158 B2 | 2/2004 | Polak | |
| 6,711,423 B2 | 3/2004 | Colvin | |
| 6,731,976 B2 | 5/2004 | Penn et al. | |
| RE38,525 E | 6/2004 | Stanley et al. | |
| 6,766,183 B2 | 7/2004 | Walsh | |
| 6,771,993 B2 | 8/2004 | Rule et al. | |
| 6,800,451 B2 | 10/2004 | Daniloff et al. | |
| 6,804,544 B2 | 10/2004 | Van Antwerp et al. | |
| 6,814,490 B1 | 11/2004 | Suhm et al. | |
| 6,815,162 B2 | 11/2004 | Boukherroub et al. | |
| 6,835,553 B2 | 12/2004 | Han et al. | |
| 6,855,556 B2 | 2/2005 | Amiss et al. | |
| 6,875,208 B2 | 4/2005 | Santini, Jr. et al. | |
| 6,885,881 B2 | 4/2005 | Leonhardt | |
| 6,885,883 B2 | 4/2005 | Parris et al. | |
| 6,893,545 B2 | 5/2005 | Gotoh et al. | |
| 6,912,078 B2 | 6/2005 | Kudrle et al. | |
| 6,918,873 B1 | 7/2005 | Millar et al. | |
| 6,928,325 B2 | 8/2005 | Zhu et al. | |
| 6,937,900 B1 | 8/2005 | Pianca et al. | |
| 6,944,488 B2 | 9/2005 | Roberts | |
| 6,952,603 B2 | 10/2005 | Gerber et al. | |
| 6,957,094 B2 | 10/2005 | Chance et al. | |
| 6,976,982 B2 | 12/2005 | Santini, Jr. et al. | |
| 6,978,182 B2 | 12/2005 | Mazar et al. | |
| 7,016,714 B2 | 3/2006 | Colvin, Jr. et al. | |
| 7,039,446 B2 | 5/2006 | Ruchti et al. | |
| 7,070,590 B2 | 7/2006 | Santini, Jr. et al. | |
| 7,107,086 B2 | 9/2006 | Reihl et al. | |
| 7,133,710 B2 | 11/2006 | Acosta et al. | |
| 7,134,999 B2 | 11/2006 | Brauker et al. | |
| 7,164,948 B2 | 1/2007 | Struble et al. | |
| 7,166,871 B2 | 1/2007 | Erchak | |
| 7,174,212 B1 | 2/2007 | Klehn et al. | |
| 7,225,024 B2 | 5/2007 | Zhu et al. | |
| 7,236,821 B2 | 6/2007 | Cates et al. | |
| 7,410,616 B2 | 8/2008 | Santini, Jr. et al. | |
| 7,447,533 B1 | 11/2008 | Fang et al. | |
| 7,449,246 B2 | 11/2008 | Kim et al. | |
| 7,450,980 B2 | 11/2008 | Kawanishi | |
| 7,471,290 B2 | 12/2008 | Wang et al. | |
| 7,577,470 B2 | 8/2009 | Shah et al. | |
| 7,632,234 B2 | 12/2009 | Manda et al. | |
| 7,633,356 B2 | 12/2009 | Hamet et al. | |
| 7,686,762 B1 | 3/2010 | Najafi et al. | |

(56) References Cited

U.S. PATENT DOCUMENTS

| | | |
|---|---|---|
| 7,761,130 B2 | 7/2010 | Simpson et al. |
| 7,805,174 B2 | 9/2010 | Carpenter et al. |
| 7,809,441 B2 | 10/2010 | Kane et al. |
| 7,829,147 B2 | 11/2010 | Aitken et al. |
| 7,890,171 B2 | 2/2011 | Zhu et al. |
| 7,894,884 B2 | 2/2011 | Song et al. |
| 8,126,554 B2 | 2/2012 | Kane et al. |
| 8,131,364 B2 | 3/2012 | Zhu et al. |
| 8,141,489 B2 | 3/2012 | Belanger et al. |
| 8,160,670 B2 | 4/2012 | Ouyang et al. |
| 8,165,840 B2 | 4/2012 | Hatlestad et al. |
| 8,257,067 B2 | 9/2012 | Fukui et al. |
| 8,290,592 B2 | 10/2012 | Michael et al. |
| 8,303,511 B2 | 11/2012 | Eigler et al. |
| 8,378,453 B2 | 2/2013 | Fedorov et al. |
| 8,414,489 B2 | 4/2013 | Shah et al. |
| 8,435,604 B2 | 5/2013 | Aitken et al. |
| 8,527,067 B2 | 9/2013 | De Kock et al. |
| 8,571,659 B2 | 10/2013 | Kane et al. |
| 8,636,884 B2 | 1/2014 | Feldman et al. |
| 8,710,625 B2 | 4/2014 | Fedorov et al. |
| 8,765,060 B2 | 7/2014 | Buhlmann et al. |
| 8,827,899 B2 | 9/2014 | Farr et al. |
| 9,101,277 B2 | 8/2015 | Doerr |
| 9,326,707 B2 * | 5/2016 | McGarraugh ...... A61B 5/14532 |
| 9,357,968 B2 | 6/2016 | Hauer et al. |
| 9,399,076 B2 | 7/2016 | Yu et al. |
| 9,693,714 B2 | 7/2017 | Dehennis et al. |
| 10,194,808 B1 * | 2/2019 | Thompson ............ A61B 5/681 |
| 10,667,745 B2 | 6/2020 | Anker et al. |
| 10,952,621 B2 | 3/2021 | Kane et al. |
| 11,089,983 B2 | 8/2021 | Li et al. |
| 11,129,557 B2 | 9/2021 | Li et al. |
| 2002/0016535 A1 | 2/2002 | Martin et al. |
| 2002/0026108 A1 | 2/2002 | Colvin |
| 2002/0033260 A1 | 3/2002 | Lungwitz et al. |
| 2002/0033454 A1 | 3/2002 | Cheng et al. |
| 2002/0035317 A1 | 3/2002 | Cheng et al. |
| 2002/0095075 A1 | 7/2002 | Madarasz et al. |
| 2002/0127626 A1 | 9/2002 | Daniloff et al. |
| 2002/0151812 A1 | 10/2002 | Scheiner et al. |
| 2003/0100040 A1 | 5/2003 | Bonnecaze et al. |
| 2003/0114735 A1 | 6/2003 | Silver et al. |
| 2003/0191376 A1 | 10/2003 | Samuels et al. |
| 2003/0208113 A1 | 11/2003 | Mault et al. |
| 2004/0023317 A1 | 2/2004 | Motamedi et al. |
| 2004/0030365 A1 | 2/2004 | Rubin |
| 2004/0059206 A1 | 3/2004 | Braig et al. |
| 2004/0073100 A1 | 4/2004 | Ballerstadt et al. |
| 2004/0087842 A1 | 5/2004 | Lakowicz et al. |
| 2004/0100376 A1 | 5/2004 | Lye et al. |
| 2004/0106953 A1 | 6/2004 | Yomtov et al. |
| 2004/0132172 A1 | 7/2004 | Cunningham et al. |
| 2004/0133079 A1 | 7/2004 | Mazar et al. |
| 2004/0147034 A1 | 7/2004 | Gore et al. |
| 2004/0161853 A1 | 8/2004 | Yang et al. |
| 2004/0176669 A1 | 9/2004 | Colvin, Jr. |
| 2004/0180379 A1 | 9/2004 | Van Duyne et al. |
| 2004/0180391 A1 | 9/2004 | Gratzl et al. |
| 2004/0186359 A1 | 9/2004 | Beaudoin et al. |
| 2004/0199062 A1 | 10/2004 | Petersson et al. |
| 2004/0206916 A1 | 10/2004 | Colvin, Jr. et al. |
| 2004/0215134 A1 | 10/2004 | Soykan et al. |
| 2004/0249311 A1 | 12/2004 | Haar et al. |
| 2004/0254438 A1 | 12/2004 | Chuck et al. |
| 2004/0260162 A1 | 12/2004 | Rohleder et al. |
| 2005/0027176 A1 | 2/2005 | Xie |
| 2005/0033133 A1 | 2/2005 | Kraft |
| 2005/0038329 A1 | 2/2005 | Morris et al. |
| 2005/0042704 A1 | 2/2005 | Alarcon et al. |
| 2005/0043894 A1 | 2/2005 | Fernandez |
| 2005/0065464 A1 | 3/2005 | Talbot et al. |
| 2005/0065556 A1 | 3/2005 | Reghabi et al. |
| 2005/0070768 A1 | 3/2005 | Zhu et al. |
| 2005/0070770 A1 | 3/2005 | Dirac et al. |
| 2005/0070771 A1 | 3/2005 | Rule et al. |
| 2005/0096587 A1 | 5/2005 | Santini et al. |
| 2005/0107677 A1 | 5/2005 | Ward et al. |
| 2005/0113657 A1 | 5/2005 | Alarcon et al. |
| 2005/0113658 A1 | 5/2005 | Jacobson et al. |
| 2005/0130249 A1 | 6/2005 | Parris et al. |
| 2005/0137481 A1 | 6/2005 | Sheard et al. |
| 2005/0148832 A1 | 7/2005 | Reghabi et al. |
| 2005/0149139 A1 | 7/2005 | Plicchi et al. |
| 2005/0154272 A1 | 7/2005 | Dirac et al. |
| 2005/0221276 A1 | 10/2005 | Rozakis et al. |
| 2005/0221277 A1 | 10/2005 | Kawanishi |
| 2005/0228226 A1 | 10/2005 | Muckner |
| 2006/0025748 A1 | 2/2006 | Ye |
| 2006/0076236 A1 | 4/2006 | Shah et al. |
| 2006/0217771 A1 | 9/2006 | Soykan et al. |
| 2006/0229694 A1 | 10/2006 | Schulman et al. |
| 2006/0253043 A1 | 11/2006 | Zhang et al. |
| 2007/0027495 A1 | 2/2007 | Gerber |
| 2007/0118056 A1 | 5/2007 | Wang et al. |
| 2007/0219628 A1 | 9/2007 | Shanley et al. |
| 2007/0252713 A1 | 11/2007 | Rondoni et al. |
| 2007/0270674 A1 | 11/2007 | Kane et al. |
| 2007/0270675 A1 | 11/2007 | Kane et al. |
| 2007/0275035 A1 | 11/2007 | Herman et al. |
| 2008/0033260 A1 | 2/2008 | Sheppard et al. |
| 2008/0046080 A1 | 2/2008 | Vanden et al. |
| 2008/0077190 A1 | 3/2008 | Kane |
| 2008/0082001 A1 | 4/2008 | Hatlestad et al. |
| 2008/0152283 A1 | 6/2008 | Nielsen et al. |
| 2008/0294209 A1 | 11/2008 | Thompson et al. |
| 2009/0018425 A1 | 1/2009 | Ouyang et al. |
| 2009/0024045 A1 | 1/2009 | Prakash et al. |
| 2009/0076353 A1 | 3/2009 | Carpenter et al. |
| 2009/0124875 A1 | 5/2009 | Bentsen et al. |
| 2009/0221885 A1 | 9/2009 | Hall et al. |
| 2009/0312973 A1 | 12/2009 | Hatlestad et al. |
| 2010/0057057 A1 | 3/2010 | Hayter et al. |
| 2010/0149544 A1 | 6/2010 | Ghislain |
| 2010/0280578 A1 | 11/2010 | Skelton et al. |
| 2010/0292634 A1 * | 11/2010 | Kircher, Jr. ......... A61M 5/1723 604/66 |
| 2011/0024307 A1 | 2/2011 | Simpson et al. |
| 2011/0098547 A1 | 4/2011 | Zhu et al. |
| 2011/0130666 A1 | 6/2011 | Dong et al. |
| 2013/0060105 A1 | 3/2013 | Shah et al. |
| 2013/0150689 A1 | 6/2013 | Shaw-klein |
| 2013/0184599 A1 * | 7/2013 | Friedman ............ A61B 5/14532 600/509 |
| 2013/0197332 A1 | 8/2013 | Lucisano et al. |
| 2013/0338727 A1 | 12/2013 | Mokelke et al. |
| 2014/0018644 A1 | 1/2014 | Colvin et al. |
| 2014/0091945 A1 | 4/2014 | Rivas et al. |
| 2014/0155710 A1 | 6/2014 | Rowland et al. |
| 2014/0276164 A1 | 9/2014 | Thakur et al. |
| 2014/0286875 A1 | 9/2014 | Gamsey et al. |
| 2014/0357964 A1 | 12/2014 | Wisniewski et al. |
| 2014/0364758 A1 * | 12/2014 | Schindhelm ....... A61B 10/0051 600/531 |
| 2015/0057509 A1 | 2/2015 | Huffstetler et al. |
| 2015/0164383 A1 | 6/2015 | Varsavsky et al. |
| 2015/0352229 A1 | 12/2015 | Brill et al. |
| 2016/0363550 A1 * | 12/2016 | Koo ..................... H04W 4/80 |
| 2016/0374597 A1 * | 12/2016 | Stahmann ........... A61B 5/7221 600/309 |
| 2017/0000359 A1 | 1/2017 | Kohli et al. |
| 2017/0215732 A1 | 8/2017 | Genier et al. |
| 2017/0245788 A1 | 8/2017 | Heikenfeld |
| 2018/0055426 A1 | 3/2018 | Kane et al. |
| 2018/0153451 A1 * | 6/2018 | Heikenfeld ........ A61B 10/0064 |
| 2018/0263511 A1 * | 9/2018 | Burnes ................... A61B 5/746 |
| 2018/0344218 A1 | 12/2018 | Li et al. |
| 2018/0350468 A1 | 12/2018 | Friedman et al. |
| 2019/0029567 A1 | 1/2019 | Stahmann et al. |
| 2019/0059792 A1 | 2/2019 | Kane et al. |
| 2019/0125228 A1 | 5/2019 | Kane et al. |
| 2019/0167112 A1 | 6/2019 | Kane et al. |

(56) References Cited

U.S. PATENT DOCUMENTS

| | | | |
|---|---|---|---|
| 2019/0167162 | A1 | 6/2019 | Li et al. |
| 2019/0336050 | A1 | 11/2019 | Deck et al. |

FOREIGN PATENT DOCUMENTS

| | | |
|---|---|---|
| EP | 3492014 | 6/2019 |
| JP | 2005287762 | 10/2005 |
| JP | 2005315871 | 11/2005 |
| JP | 2006507078 | 3/2006 |
| JP | 2006126715 | 5/2006 |
| JP | 2007525858 | 9/2007 |
| JP | 2009537247 | 10/2009 |
| WO | 9625978 | 8/1996 |
| WO | 9719188 | 5/1997 |
| WO | 9801071 | 1/1998 |
| WO | 9902651 | 1/1999 |
| WO | 0018289 | 4/2000 |
| WO | 0025862 | 5/2000 |
| WO | 0025863 | 5/2000 |
| WO | 0180728 | 11/2001 |
| WO | 2004039265 | 5/2004 |
| WO | 2004071291 | 8/2004 |
| WO | 2004081522 | 9/2004 |
| WO | 2004091719 | 10/2004 |
| WO | 2004092713 | 10/2004 |
| WO | 2005074612 | 8/2005 |
| WO | 2006017169 | 2/2006 |
| WO | 2007110867 | 10/2007 |
| WO | 2007137037 | 11/2007 |
| WO | 2008076491 | 6/2008 |
| WO | 2009038996 | 3/2009 |
| WO | 2013016573 | 1/2013 |
| WO | 2015048514 | 4/2015 |
| WO | 2019023093 | 1/2019 |

OTHER PUBLICATIONS

Non-Final Office Action for U.S. Appl. No. 16/136,773 dated Jun. 1, 2020 (43 pages).
Non-Final Office Action for U.S. Appl. No. 16/136,875 dated May 27, 2020 (43 pages).
International Search Report and Written Opinion for PCT Application No. PCT/US2018/043225 dated Nov. 16, 2018 (11 pages).
International Search Report and Written Opinion for PCT Application No. PCT/US2018/047549 dated Oct. 26, 2018 (15 pages).
Extended European Search Report for European Patent Application No. 18202201.2 dated Jun. 28, 2019 (9 pages).
Response to Communication Pursuant to Rule 69 EPC for European Patent Application No. 18174561.3 filed Jun. 3, 2019 (21 pages).
Anderson, J. M. et al., "Monocyte, Macrophage and foreign body giant cell interactions with molecularly engineered surfaces," Journal of Materials Science: Materials in Medicine 10 (1999) 579-588 (10 pages).
Anderson, James M. "Biological Responses to Materials," Annu. Rev. Mater. Res. 2001. 31:81-110 (30 pages).
Anderson, James M. et al., "Foreign Body Reaction to Biomaterials," Semin. Immunol. Apr. 2008; 20(2): 86-100 (27 pages).
Bakker, Eric et al., "Carrier-Based Ion-Selective Electrodes and Bulk Optodes. 1. General Characteristics," Chem. Rev. 1997, 97, 3083-3132 (50 pages).
Benco, John S. et al., "Optical Sensors for Blood Analytes," The Spectrum, vol. 14, Issue 4, pp. 4-11, Winter 2001 (8 pages).
Bender, J. W. et al., "The Use of Biomedical Sensors to Monitor Capsule Formation Around Soft Tissue Implants," Annals of Plastic Surgery, vol. 56, No. 1, Jan. 2006, pp. 72-77 (6 pages).
Bridges, Amanda W. et al., "Anti-Inflammatory Polymeric Coatings for Implantable Biomaterials and Devices," Journal of Diabetes Science and Technology 2008;2(6):984-994 (11 pages).
Buhlmann, Philippe et al., "Carrier-Based Ion-Selective Electrodes and Bulk Optodes. 2. Ionophores for Potentiometric and Optical Sensors," Chem. Rev. 1998, 98, 1593-1687 (95 pages).

"Communication Pursuant to Article 94(3) EPC," for European Patent Application No. 07762189.4 dated Mar. 24, 2009 (3 pages).
"Communication pursuant to Article 94(3) EPC," for European Patent Application No. 07762189.4 dated Mar. 16, 2010 (3 pages).
"Extended European Search Report," for European Patent Application No. 18174561.3 dated Aug. 28, 2018 (9 pages).
File History for U.S. Appl. No. 11/383,926.
File History for U.S. Appl. No. 11/383,933.
File History for U.S. Appl. No. 11/856,850.
File History for U.S. Appl. No. 12/391,761.
"First Examination Report," for Australian Patent Application No. 2008302499 dated Feb. 8, 2011 (1 page).
Han, In S. et al., "Constant-Volume Hydrogel Osmometer: A New Device Concept for Miniature Biosensors," Biomacromolecules, Mar. 2002, pp. 1271-1275 (5 pages).
He, Huarui et al., "Enantioselective Optodes," Analytica Chimica Acta, 246, pp. 251-257, 1991 (7 pages).
He, Wei et al., "A Novel Anti-inflammatory Surface for Neural Electrodes," Adv. Mater. 2007, 19, 3529-3533 (5 pages).
Helton, Kristen L. et al., "Biomechanics of the Sensor-Tissue Interface-Effects of Motion, Pressure, and Design on Sensor Performance and the Foreign Body Response—Part I: Theoretical Framework," Journal of Diabetes Science and Technology 2011;5(3):632-646 (15 pages).
"International Preliminary Report on Patentability," for PCT Application No. PCT/US2008/075673 dated Mar. 24, 2010 (6 pages).
"International Search Report and Written Opinion," for PCT Application No. PCT/US2008/075673 dated Nov. 28, 2008 (13 pages).
Koh, Ahyeon et al., "Glucose Sensor Membranes for Mitigating the Foreign Body Response," Journal of Diabetes Science and Technology 2011;5(5):1052-1059 (8 pages).
Koronczi, et al., "Development of a submicron optochemical potassium sensor with enhanced stability due to internal reference," Sensors and Actuators B, 51:188-195 (1998).
Kuwana, Eddy et al., "Sensing of pH in Multiply Scattering Media with Fluorescence Lifetime," Advanced Biomedical and Clinical Diagnostic Systems, Proceedings of SPIE, vol. 4958, pp. 32-42, 2003 (11 pages).
Lehn, J. M. et al., "[2]—Cryptates: Stability and Selectivity of Alkali and Akaline-Earth Macrobicycle Complexes," Journal of the American Chemical Society, Nov. 12, 1975 pp. 6700-6707 (8 pages).
Lima-Oliveira, Gabriel et al., "Patient Posture for Blood Collection by Venipuncture: Recall for Standardization After 28 Years," Brazilian Journal of Hematology and Hemotherapy 2017 <http://dx.doi.org/10.1016/j.bjhh.2017.01.004> (6 pages).
Messier, "The Joining of Materials," Nov. 2004 (58 pages).
"Microminiature Device Monitors Vital Electrolytes and Metabolites," John Glenn Biomedical Engineering Consortium, May 2002 (2 pages).
"Microminiature Monitor for Vital Electrolyte and Metabolite Levels of Astronauts—Status Report," John Glenn Biomedical Engineering Consortium NASA Glenn Research Center at Lewis Field, Apr. 2003 (5 pages). NASA Glenn Research Center at Lewis Field.
Novak, Matthew T. et al., "Modeling the relative impact of capsular tissue effects on implanted glucose sensor time lag and signal attenuation," Anal. Bioanal. Chem. Oct. 2010; 398(4):1695-1705 (22 pages).
"Office Action," for Japanese Patent Application No. 2010-524940 dated Nov. 22, 2011 (8 pages) with English translation.
Padmanabhan, Jagnnath et al., "Nanomaterials, Inflammation and Tissue Engineering," Wiley Interdiscip Rev Nanomed Nanobiotechnol. May 2015;7(3):355-370 (23 pages).
"PCT International Search Report and Written Opinion," for International Application No. PCT/US2007/068954, dated Nov. 17, 2008 (12 pages).
"Response to Communication Pursuant to Article 94(3) EPC," for European Patent Application No. 07762189.4 filed with the EPO Jul. 27, 2009 (9 pages).
Roger, Yvonne et al., "Grid-like surface structures in thermoplastic polyurethane induce anti-inflammatory and anti-fibrotic processes

(56) References Cited

OTHER PUBLICATIONS in bone marrow-derived mesenchymal stem cells," ABSTRACT ONLY Colloids and Surfaces B Biointerfaces vol. 148, Dec. 2016, pp. 104-115 (4 pages).
Seelig, Mildred S. "Electrographic Patterns of Magnesium Depletion Appearing in Alcoholic Heart Disease," Annals of the New York Academy of Sciences, vol. 162, Article 2, 1969, pp. 906-917 (13 pages).
Sharkawy, A. A. et al., "Engineering the tissue which encapsulates subcutaneous implants. I. Diffusion properties," Department of Biomedical Engineering, NSF Center for Emerging Cardiovascular Technology, Duke University, Durham, North Carolina 1996 (12 pages).
Shirreffs, S. M. "The Effect of Posture Change on Blood Volume, Serum Potassium, and Whole Body Electrical Impedance," Eur. J. Appl. Physiol. (1994)69:461-463 (3 pages).
Tohda, Koji et al., "A Microscopic, Continuous, Optical Monitor for Interstitial Electrolytes and Glucose," Chemphyschem 2003, pp. 155-160 (6 pages).
Tohda, Koji et al., "Micro-miniature Autonomous Optical Sensor Array for Monitoring Ions and Metabolites 1: Design, Fabrication, and Data Analysis," Analytical Sciences, Mar. 2006, vol. 22 pp. 383-388 (6 pages).
Tsai, Hc et al., "Simultaneous Determination of Renal Clinical Analytes in Serum using Hydrolase- and Oxidase-Encapsulated Optical Array Biosensors," Analytical Biochemistry 334 (2004) 183-192 (10 pages).
"Upconverting nanoparticles," Wikipeda.com accessed Jun. 12, 2017 (13 pages).
Voskerician, Gabriela et al., "Biocompatibility and Biofouling of MEMs Drug Delivery Devices," Biomaterials 24 (2003) 1959-1967 (9 pages).
Weisberg, Lawrence S. "Management of Severe Hyperkalemia," Crit Care Med 2008 vol. 36, No. 12 (6 pages).
Partial European Search Report for European Patent Application No. 18188253.1 dated Jan. 7, 2019 (11 pages).
Extended European Search Report for European Patent Application No. 18188253.1 dated Apr. 9, 2019 (10 pages).
Extended European Search Report for European Patent Application No. 18207668.7 dated Apr. 3, 2019 (7 pages).
Extended European Search Report for European Patent Application No. 18209525.7 dated Feb. 27, 2019 (12 pages).
Communication Pursuant to Article 94(3) EPC for European Patent Application No. 18174561.3 dated Jan. 27, 2020 (5 pages).
International Preliminary Report on Patentability for PCT Application No. PCT/US2018/043225 dated Feb. 6, 2020 (7 pages).
International Preliminary Report on Patentability for PCT Application No. PCT/US2018/047549 dated Mar. 5, 2020 (11 pages).
Response to Communication Pursuant to Rule 69 EPC for European Patent Application No. 18202201.2 filed Jan. 31, 2020 (22 pages).
Response to Communication Pursuant to Rule 69 EPC for European Patent Application No. 18209525.7 filed with the EPO Dec. 12, 2019 (33 pages).
Response to European Search Report for European Patent Application No. 18188253.1 filed Nov. 7, 2019 (14 pages).
Response to Extended European Search Report for European Patent Application No. 18207668.7 filed Nov. 29, 2019 (14 pages).
Non-Final Office Action for U.S. Appl. No. 16/041,923 dated Jul. 23, 2020 (61 pages).
Response to Non-Final Rejection dated May 27, 2020 for U.S. Appl. No. 16/136,875, submitted via EFS-Web on Jul. 22, 2020, 11 pages.
Response to Non-Final Rejection dated May 5, 2020 for U.S. Appl. No. 15/992,823, submitted via EFS-Web on Jul. 7, 2020, 10 pages.
Communication Pursuant to Article 94(3) EPC for European Patent Application No. 18207668.7 dated Aug. 4, 2020 (5 pages).
Final Office Action for U.S. Appl. No. 15/992,823 dated Aug. 13, 2020 (18 pages).
Final Office Action for U.S. Appl. No. 16/136,875 dated Aug. 21, 2020 (10 pages).
Non-Final Office Action dated May 27, 2020 for U.S. Appl. No. 16/136,875, 43 pages.
Response to Communication Pursuant to Article 94(3) EPC for European Patent Application No. 18174561.3 filed Jul. 27, 2020 (11 pages).
Response to Non-Final Rejection dated Jun. 1, 2020 for U.S. Appl. No. 16/136,773, submitted via EFS-Web on Aug. 20, 2020, 10 pages.
Communication Pursuant to Article 94(3) EPC for European Patent Application No. 18207668.7 dated Jan. 13, 2021 (4 pages).
Communication Pursuant to Article 94(3) EPC for European Patent Application No. 18209525.7 dated Dec. 8, 2020 (5 pages).
Non-Final Office Action for U.S. Appl. No. 15/992,823 dated Dec. 23, 2020 (18 pages).
Non-Final Office Action for U.S. Appl. No. 16/041,923 dated Feb. 2, 2021 (39 pages).
Non-Final Office Action for U.S. Appl. No. 16/106,623 dated Oct. 9, 2020 (60 pages).
Non-Final Office Action for U.S. Appl. No. 16/136,875 dated Jan. 25, 2021 (12 pages).
Notice of Allowance for U.S. Appl. No. 16/136,773 dated Nov. 18, 2020 (17 pages).
Response to Communication Pursuant to Article 94(3) EPC for European Patent Application No. 18207668.7 filed Dec. 11, 2020 (65 pages).
Response to Communication Pursuant to Rules 161(1) and 162 EPC for European Patent Application No. 18773017.1 filed Sep. 30, 2020 (13 pages).
Response to Final Rejection dated Aug. 13, 2020 for U.S. Appl. No. 15/992,823, submitted via EFS-Web on Oct. 13, 2020, 9 pages.
Response to Final Rejection dated Aug. 21, 2020 and Advisory Action dated Oct. 19, 2020 for U.S. Appl. No. 16/136,875, submitted via EFS-Web on Nov. 20, 2020, 14 pages.
Response to Final Rejection dated Aug. 21, 2020 for U.S. Appl. No. 16/136,875, submitted via EFS-Web on Oct. 13, 2020, 12 pages.
Response to Non-Final Rejection dated Jul. 23, 2020 for U.S. Appl. No. 16/041,923, submitted via EFS-Web on Oct. 13, 2020, 12 pages.
Response to Non-Final Rejection dated Oct. 9, 2020 for U.S. Appl. No. 16/106,623, submitted via EFS-Web on Jan. 8, 2021, 21 pages.
"Notice of Allowance," for U.S. Appl. No. 15/992,823 dated Jun. 10, 2021 (16 pages).
"Notice of Allowance," for U.S. Appl. No. 16/136,875 dated Apr. 15, 2021 (13 pages).
"Response to Communication Pursuant to Article 94(3) EPC," for European Patent Application No. 18209525.7 filed Apr. 15, 2021 (10 pages).
"Response to Non-Final Rejection," dated Dec. 23, 2020 for U.S. Appl. No. 15/992,823, submitted via EFS-Web on Mar. 23, 2021, 9 pages.
"Response to Non-Final Rejection," dated Feb. 2, 2021 for U.S. Appl. No. 16/041,923, submitted via EFS-Web on Mar. 17, 2021, 12 pages.
"Response to Non-Final Rejection," dated Jan. 25, 2021 for U.S. Appl. No. 16/136,875, submitted via EFS-Web on Mar. 17, 2021, 12 pages.
"Final Office Action," for U.S. Appl. No. 16/041,923 dated Jul. 9, 2021 (29 pages).
"Non-Final Office Action," for U.S. Appl. No. 16/041,923 dated Nov. 15, 2021 (21 pages).
"Non-Final Office Action," for U.S. Appl. No. 16/106,623 dated Aug. 25, 2021 (31 pages).
"Non-Final Office Action," for U.S. Appl. No. 16/130,638 dated Aug. 23, 2021 (67 pages).
"Response to Communication Pursuant to Article 94(3) EPC," for European Patent Application No. 18207668.7 filed May 21, 2021 (32 pages).
"Response to Final Rejection," dated Jul. 9, 2021 and Advisory Action dated Sep. 20, 2021 for U.S. Appl. No. 16/041,923, submitted via EFS-Web on Sep. 27, 2021, 12 pages.
"Response to Final Rejection," dated Jul. 9, 2021 for U.S. Appl. No. 16/041,923, submitted via EFS-Web on Sep. 9, 2021, 12 pages.

(56) References Cited

OTHER PUBLICATIONS

"Response to Non-Final Rejection," dated Aug. 23, 2021 for U.S. Appl. No. 16/130,638, submitted via EFS-Web on Nov. 1, 2021, 9 pages.

"Response to Non-Final Rejection," dated Aug. 25, 2021 for U.S. Appl. No. 16/106,623, submitted via EFS-Web on Oct. 27, 2021, 14 pages.

"Final Office Action," for U.S. Appl. No. 16/106,623 dated Dec. 2, 2021 (25 pages).

"First Office Action," for Chinese Patent Application No. 201710400287.0 dated Dec. 23, 2021 (17 pages) No English Translation.

"Response to Final Rejection," dated Jan. 26, 2022 and the Advisory Action dated Apr. 18, 2022 for U.S. Appl. No. 16/130,638, submitted via EFS-Web on Apr. 26, 2022, 7 pages.

"Response to Final Rejection," dated Dec. 2, 2021 and the Advisory Action dated Apr. 5, 2022 for U.S. Appl. No. 16/106,623, submitted via EFS-Web on May 2, 2022, 14 pages.

"Final Office Action," for U.S. Appl. No. 16/130,638 dated Jan. 26, 2022 (16 pages).

"First Office Action," for Chinese Patent Application No. 201710681567.3 dated Mar. 18, 2022 (7 pages) No English Translation.

"First Office Action," for Chinese Patent Application No. 201710730979.1 dated Apr. 11, 2022 (11 pages) No English Translation.

"International Search Report and Written Opinion," for PCT Application No. PCT/US2021/056602 dated Feb. 9, 2022 (12 pages).

"Invitation to Pay Additional Fees," for PCT Application No. PCT/US2021/056590 dated Mar. 9, 2022 (9 pages).

"Response to Final Rejection," dated Jan. 26, 2022 for U.S. Appl. No. 16/130,638, submitted via EFS-Web on Mar. 24, 2022, 8 pages.

"Response to Final Rejection," dated Dec. 2, 2021 for U.S. Appl. No. 16/106,623, submitted via EFS-Web on Feb. 24, 2022, 14 pages.

"Response to Non-Final Rejection," dated Nov. 15, 2021 for U.S. Appl. No. 16/041,923, submitted via EFS-Web on Feb. 9, 2022, 7 pages.

* cited by examiner

SYSTEMS AND METHODS INCLUDING ELECTROLYTE SENSOR FUSION

This application claims the benefit of China Patent Application No. 201710681567.3, filed Aug. 10, 2017, the content of which is herein incorporated by reference in its entirety.

FIELD

Embodiments herein relate to systems and methods for combining data from different types of sensors. In particular, embodiments herein relate to systems and methods for combining data from different sensors for physiological analytes such as electrolytes.

BACKGROUND

In the context of diagnosis and monitoring of patients, clinicians frequently evaluate many different pieces of data about their patients including physical observations, descriptions of symptoms, test results, and the like. One aspect that testing can reveal is the physiological concentration of electrolytes for the patient. Electrolyte concentrations can be important to know because of their effect on various organs and bodily functions. Typically, electrolyte concentrations are assessed by drawing a fluid sample (or other sample) from the patient followed by an in vitro assay.

SUMMARY

Embodiments herein relate to systems and methods for combining data from different types of sensors. In particular, embodiments herein relate to systems and methods for combining data from different sensors for physiological analytes such as electrolytes.

In a first aspect, a medical system is included. The medical system can include a first sensor configured to produce a first value for an analyte and a second sensor different than the first sensor, the second sensor configured to produce a second value for the analyte. The system can also include a controller configured to receive the first and second values. The controller can create a blended analyte value from the first value and second value.

In a second aspect, in addition to or in place of other aspects herein, the controller creates a blended analyte value by using the first value to normalize the second value or by using the second value to normalize the first value.

In a third aspect, in addition to or in place of other aspects herein, the blended analyte value is created using a method that reduces at least one of sensor offset errors, sensor gain errors and sensor latency as compared with values from the first sensor and second sensor standing alone.

In a fourth aspect, in addition to or in place of other aspects herein, at least one of the first sensor and the second sensor is implantable.

In a fifth aspect, in addition to or in place of other aspects herein, at least one of the first sensor and the second sensor is an optical chemical sensor.

In a sixth aspect, in addition to or in place of other aspects herein, the optical chemical sensor measures one or more of an electrolyte, a protein, a sugar, a hormone, a peptide, an amino acid and a metabolic product.

In a seventh aspect, in addition to or in place of other aspects herein, the electrolyte measured is at least one of potassium, calcium, sodium, magnesium, hydrogen phosphate, chloride and bicarbonate.

In an eighth aspect, in addition to or in place of other aspects herein, an optical chemical sensor measures pH.

In a ninth aspect, in addition to or in place of other aspects herein, at least one of the first sensor and the second sensor is an ECG sensor.

In a tenth aspect, in addition to or in place of other aspects herein, the first sensor is faster reacting than the second sensor.

In an eleventh aspect, in addition to or in place of other aspects herein, the first sensor is an ECG sensor and the second sensor is a chemical sensor.

In a twelfth aspect, a medical system is included. The medical system includes a first sensor configured to produce a first value for an analyte and a second sensor different than the first sensor, the second sensor configured to produce a second value for the analyte. The system can also include a controller configured to receive the first and second values. The controller can trigger a measurement change of the second sensor based on the first value for the analyte.

In a thirteenth aspect, in addition to or in place of other aspects herein, the measurement change is selected from the group consisting of sampling frequency, measurement schedule, measurement intensity, and turning the sensor on or off.

In a fourteenth aspect, in addition to or in place of other aspects herein, the first sensor has a faster response time than the second sensor.

In a fifteenth aspect, in addition to or in place of other aspects herein, data from the first sensor is used for trend analysis of data from the second sensor.

In a sixteenth aspect, in addition to or in place of other aspects herein, data from the second sensor is used for trend analysis of data from the first sensor.

In a seventeenth aspect, in addition to or in place of other aspects herein, the controller creates a blended analyte value from the first value and second value.

In an eighteenth aspect, in addition to or in place of other aspects herein, the blended analyte value is created using a method that reduces at least one of sensor offset errors, sensor gain errors and sensor latency.

In a nineteenth aspect, in addition to or in place of other aspects herein, the first sensor is faster reacting than the second sensor.

In a twentieth aspect, in addition to or in place of other aspects herein, the first sensor is an ECG sensor and the second sensor is a chemical sensor.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

and blended values for an analyte resulting from blending the data from the first sensor and the data from the second sensor.

Figure 3:
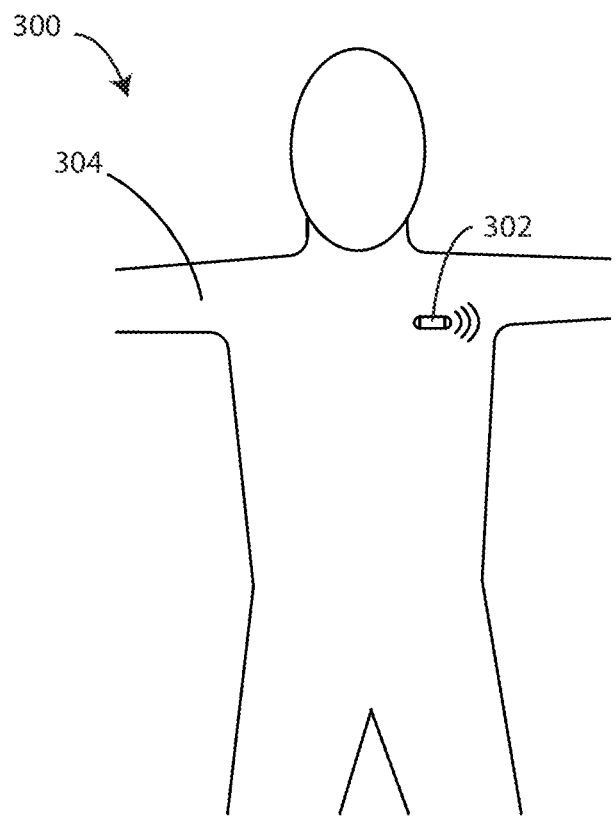

FIG. 3 is a schematic view of a medical device system implanted within a patient in accordance with various embodiments herein.

Figure 4:
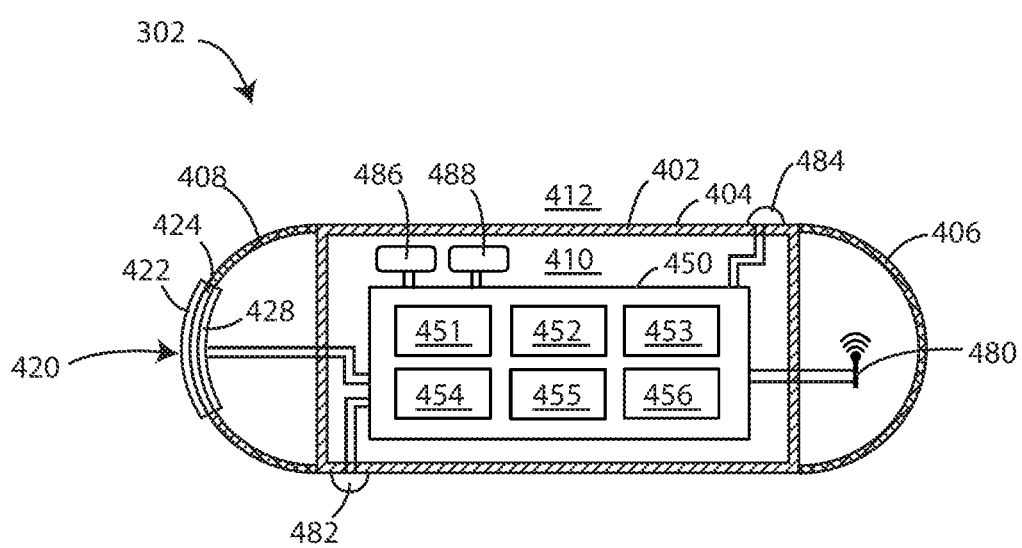

FIG. 4 is a schematic cross-sectional view of the implantable medical device shown in FIG. 3, in accordance with various embodiments herein.

Figure 5:
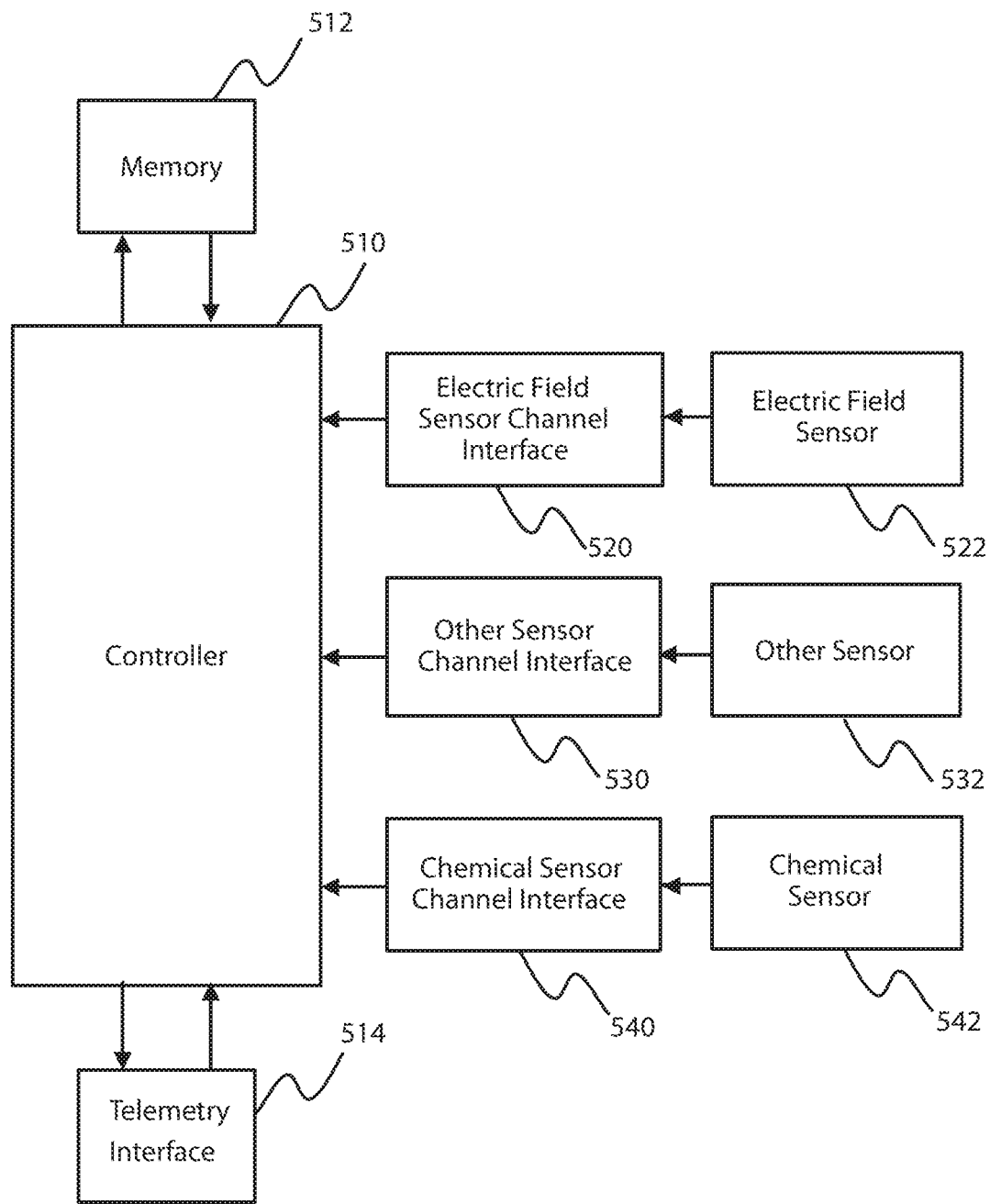

FIG. 5 is a schematic diagram of components of an implantable medical device in accordance with various embodiments herein.

Figure 6:
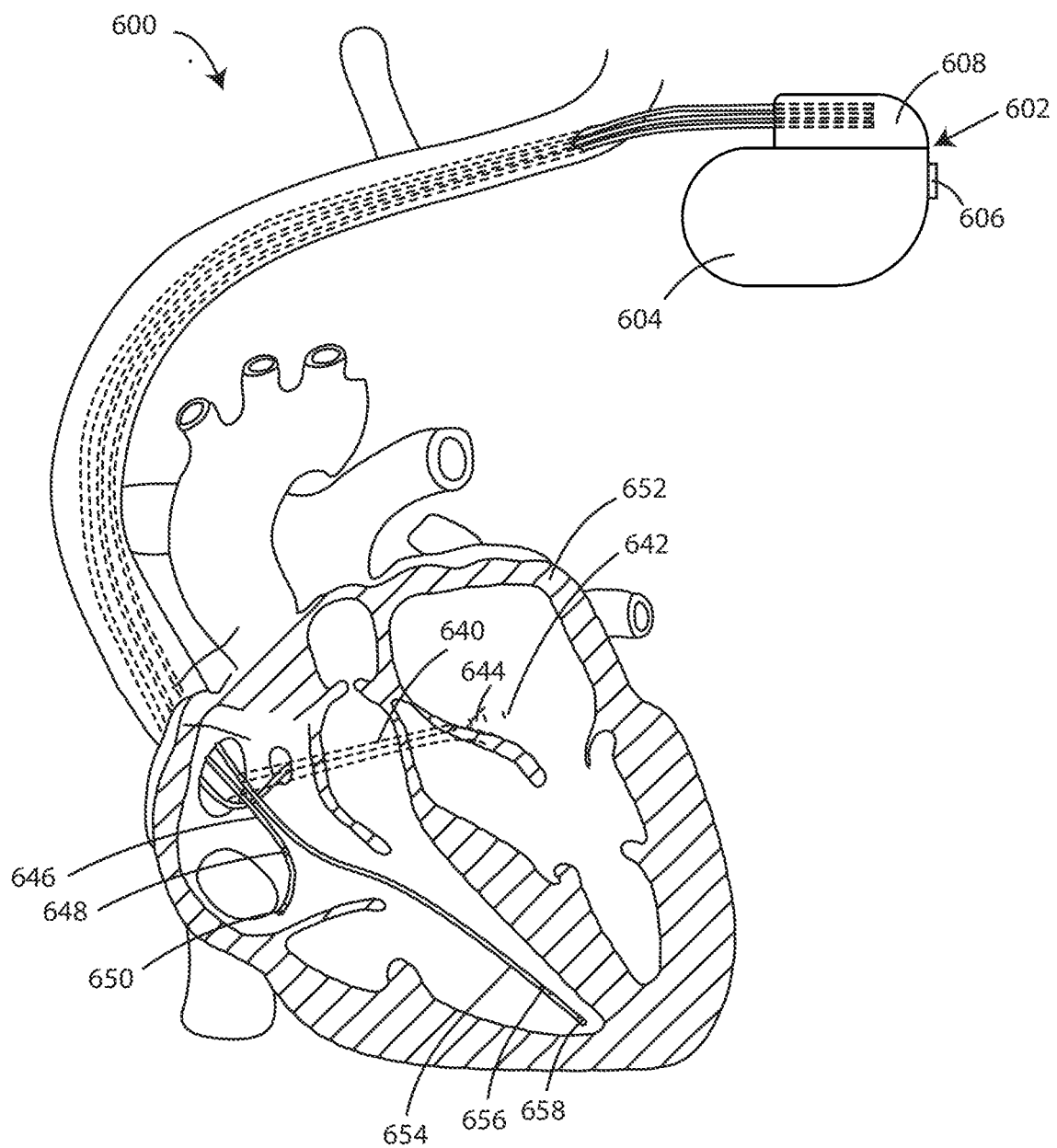

FIG. 6 is a schematic view of a medical device system in accordance with various embodiments herein.

Figure 7:
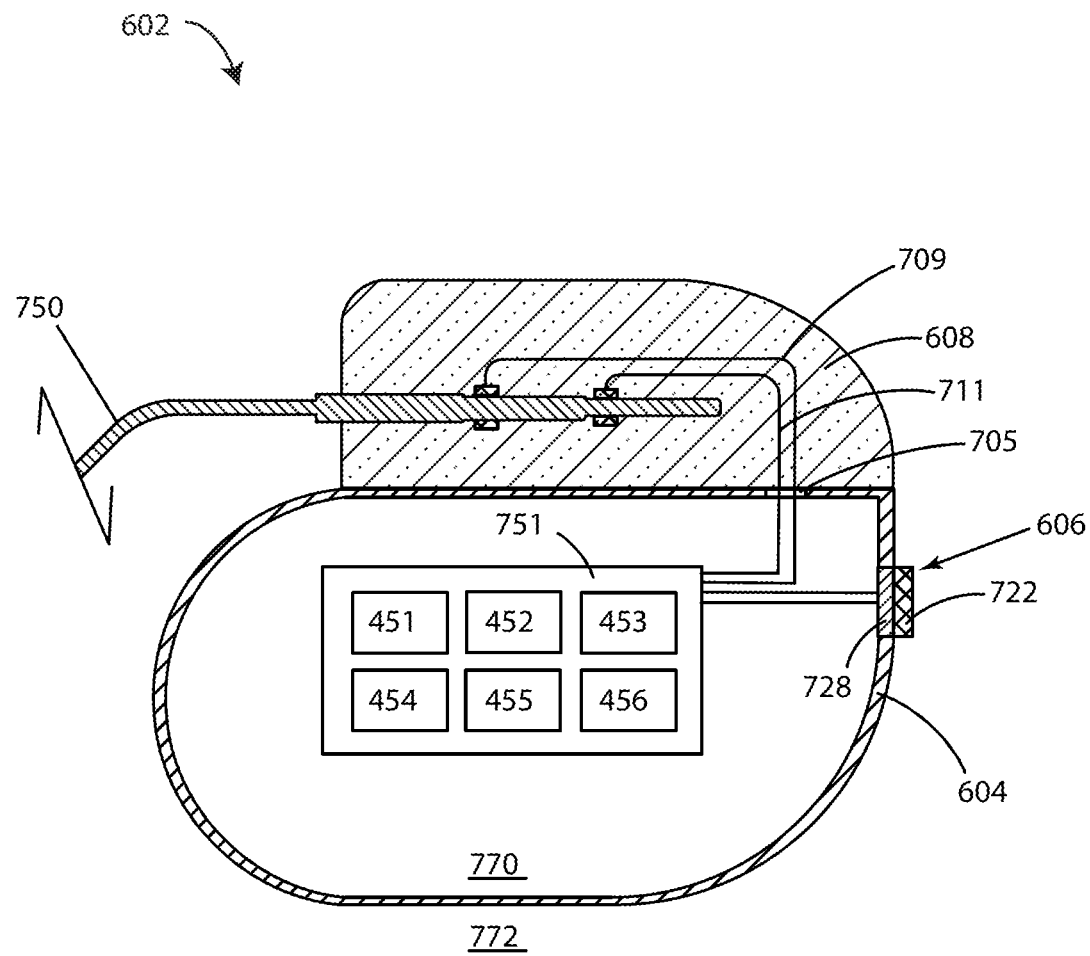

FIG. 7 is a schematic cross-sectional view of the implantable medical device shown in FIG. 6, in accordance with various embodiments herein.

Figure 8:
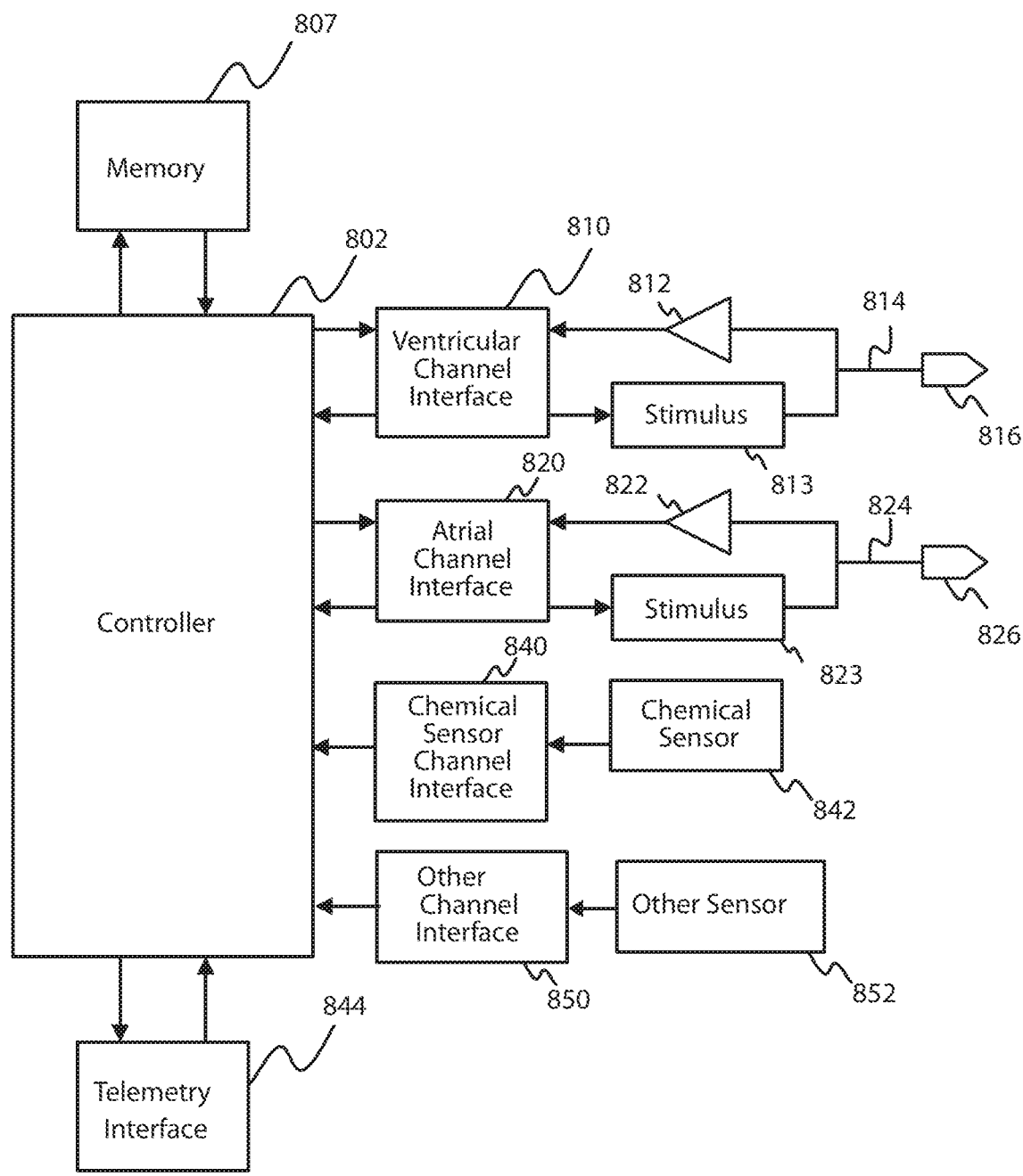

FIG. 8 is a schematic diagram of components of an implantable medical device in accordance with various embodiments herein.

Figure 9:
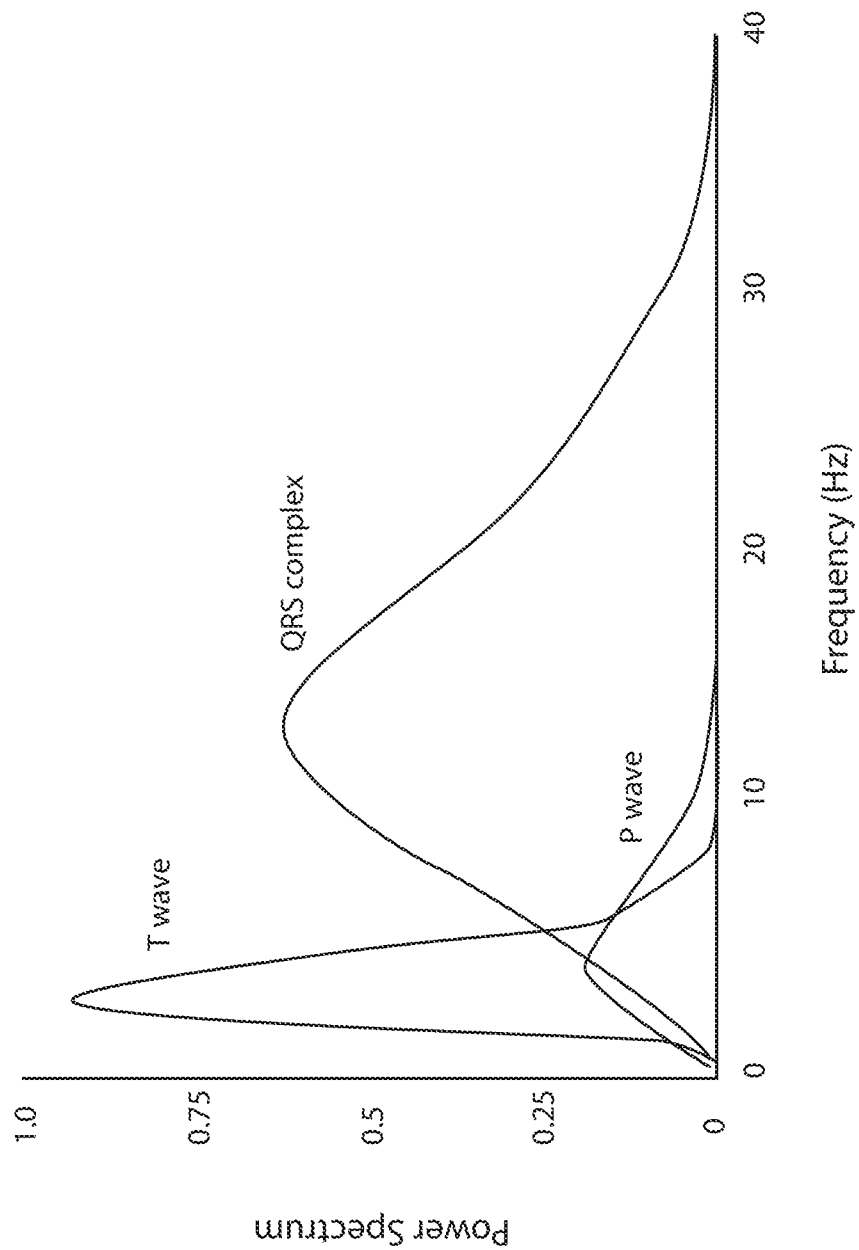

FIG. 9 is a diagram showing the frequency spectra of various ECG features.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

Electrolyte concentrations are clinically important because of their effect on various organs and bodily functions. Typically, electrolyte concentrations are assessed by drawing a fluid sample (or other sample) from the patient followed by conducting an in vitro assay on the sample. However, new sensor systems offer the promise of being able to assess electrolyte concentrations with implanted devices allowing for much more frequent assessment of electrolyte concentrations.

Unfortunately, many electrolyte sensors suffer from one type of limitation or another. For example, some electrolyte sensors have a relatively slow response time such that a sudden change in electrolyte concentrations may not be quickly reflected in the sensor data. As another example, some electrolyte sensors are relatively good at detecting a change in electrolyte concentrations, but relatively poor in determining the absolute value of the electrolyte concentration. This can result in potentially large offset errors. As yet another example of possible limitations, some fast response time sensors may not be as specific (e.g., can be confounded by other analytes—such as other electrolytes and/or non-electrolytes) as other types of sensors.

However, in accordance with various embodiments herein, data from different types of electrolyte (or other analyte) sensors can be blended together in order to benefit from the best aspects of each type of sensor while mitigating the limitations associated with each sensor type.

In an embodiment, medical systems are included herein having a first sensor configured to produce a first value for an analyte and a second sensor different than the first sensor. The second sensor can be configured to produce a second value for the analyte. The medical system can also include a controller configured to receive the first and second values and create a blended analyte value from the first value and second value.

Fast Response Time Sensors

Embodiments herein can include one or more sensors exhibiting a fast response time. For example, in various embodiments, a fast response time sensor herein can have a response time (time until a steady-state level of sensor response is achieved after a change in the intrinsic value being measured) of less than 5 minutes, 2 minutes, 60 seconds, 30 seconds, 15 seconds, 5 seconds, 3 seconds or 1 second, or an amount of time falling within a range between any of the foregoing.

In some embodiments, fast response time sensors herein can be non-invasive, such as in the context of an external sensor contacting the skin. However, in other embodiments, fast response time sensors herein can be implanted.

One exemplary fast response time sensor is an ECG sensor. ECG sensors can include electrodes in order to sense electrical phenomena (including, but not limited to, electrical potentials and changes therein) within the tissue of a patient.

Various processing steps can be taken with raw ECG sensor data in order to calculate and/or estimate analyte concentrations therefrom. In some embodiments, raw ECG sensor data can be subject to a filtering step. In some embodiments, raw ECG sensor data can be subject to a pattern matching step. In some embodiments, raw ECG sensor data can be subject to a feature analysis step. In some embodiments, raw ECG sensor data can be subject to a template matching step.

Variation in electrolyte values can result in substantial changes in ECG data. Such changes are evident when viewing a trace of ECG data (waveform) and can take the form of feature elevation, feature reduction, timing changes between characteristic features (including increased or decreased time gaps), cycle time changes (such as R to R timing, etc.) and the like.

Figure 1:
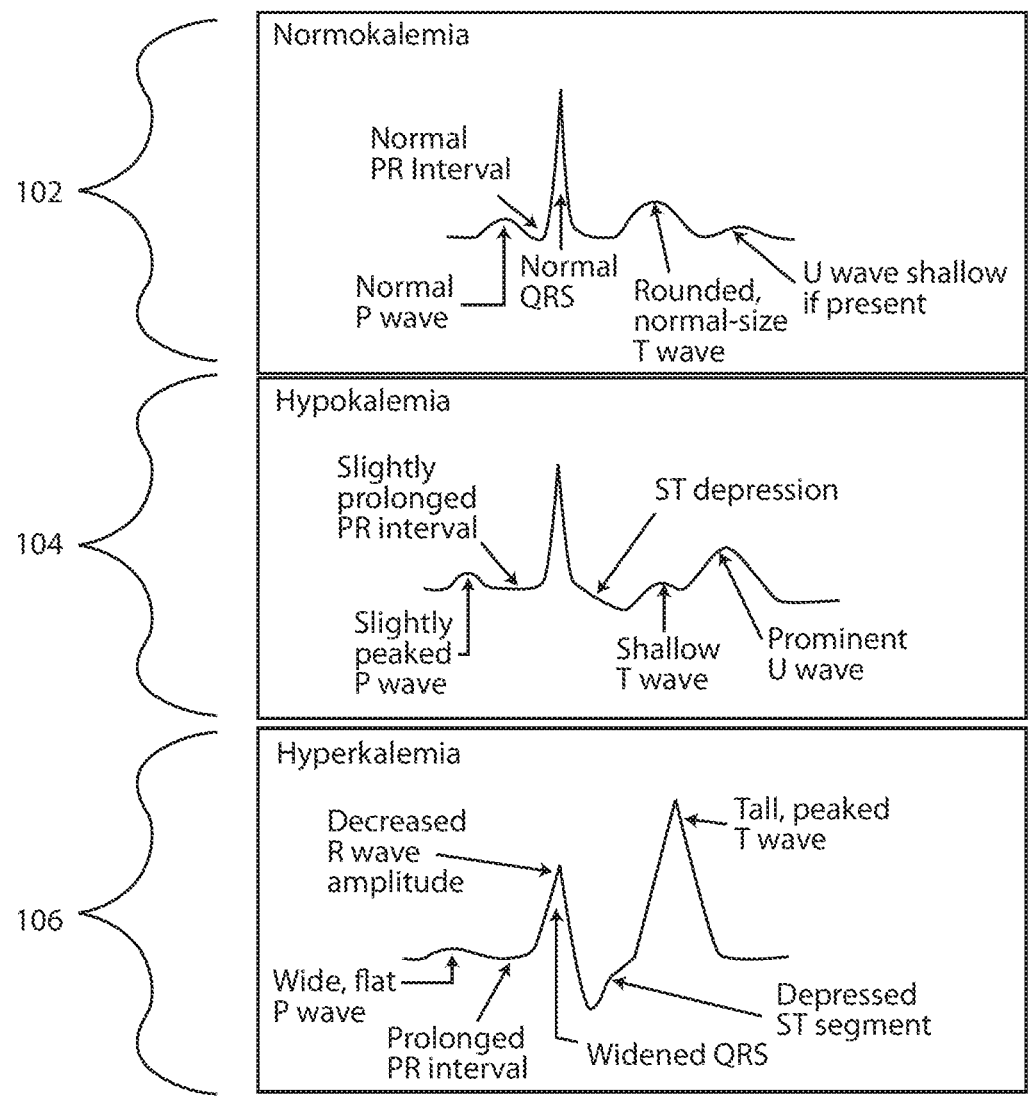
FIG. 1 shows exemplary ECG waveforms illustrating the effects that electrolyte concentrations can have on ECG waveform features.

Referring now to FIG. 1, ECG waveforms are shown illustrating the effects that electrolyte concentrations can have on the ECG waveform features. An exemplary ECG waveform for a physiologically normal concentration of potassium (normokalemia) is shown at 102. It can be seen that the P wave is normal, the PR interval is normal, the QRS complex is normal, the T wave is rounded and of a normal size, and the U wave is relatively shallow, if present.

In contrast, an exemplary ECG waveform for a physiologically abnormally low concentration of potassium (hypokalemia) is shown at 104. It can be seen that the P wave has become slightly peaked, the PR interval has become prolonged, the ST segment is depressed, the T wave has become shallow, and the U wave is now prominent.

In another example, an ECG waveform for a physiologically abnormally high concentration of potassium (hyperkalemia) is shown at 106. It can be seen that the P wave has become wide and flat, the PR interval has become prolonged, the R wave exhibits a decreased amplitude, the QRS complex is widened, the ST segment is depressed, and the T wave is now tall and peaked.

The relative magnitude of changes to the ECG waveform can be evaluated in order to estimate the concentration of potassium (in this case) responsible for causing them. As one example, the magnitude of the changes (individually or in the aggregate) can be compared with standard data gathered across a population of patients indexed for different potassium concentrations in order to estimate the current potassium concentration indicated by the currently observed ECG waveform. The concentration can then be estimated by determining which indexed waveform or set of waveforms best matches that currently being generated by evaluating the patient. As a variant of this approach, a set of templates can be used, with each template corresponding to a different specific electrolyte concentration. Then a pattern matching algorithm can be used (e.g., least squares method or another technique) in order to determine which template is the best match for the waveform currently being generated by evaluating the patient.

In some embodiments, the standard data used for comparison can be tuned or modified to be more accurate for the specific patient through a calibration procedure performed by gathering ECG data while the patient has (or is made to have) specific known physiological concentrations of potassium. In some cases, this calibration data can be stored and used to form templates specific for the individual patient. In other embodiments, it can be used to calibrate the electrolyte (or other analyte) values associated with preexisting templates or patterns.

In some embodiments filtering of the ECG can be performed and is configured to augment ECG changes associated with the change in the analyte being measured. For example, if potassium is being measured the ECG can be filtered to augment the T wave and thereby changes associated with it. In an embodiment ECG frequencies in the range of 2 to 8 Hz are filtered and amplified to augment changes in the T wave. FIG. 9 is a diagram showing the frequency spectra of various ECG features.

High-Accuracy Sensors

Embodiments herein can also include one or more sensors exhibiting high accuracy for measurement of a specific analyte compared with the fast response time sensors used with embodiments herein. Also, in some embodiments, the high-accuracy sensor can be highly specific to a particular chose electrolyte. In some embodiments, the high-accuracy sensor can provide an absolute measurement (absolute value) of the analyte concentration.

However, relative to some fast response time sensors described above, various high-accuracy sensors herein can exhibit a relatively slow response time. For example, in various embodiments, the high-accuracy sensor may have a response time (time until a steady-state level of sensor response is achieved after a change in the intrinsic value being measured) of greater than 30 seconds, 60 seconds, 2 minutes, 5 minutes, 10 minutes, 15 minutes, 20 minutes, 30, minutes, 45 minutes, 60 minutes or an amount of time falling within a range between any of the foregoing.

High-accuracy chemical sensors herein can be of various types including optical and/or optoelectronic chemical sensors. In some embodiments, the physiological concentration of an analyte is sensed directly. In other embodiments, the physiological concentration of an analyte is sensed indirectly. By way of example, a metabolite of a particular analyte can be sensed instead of the particular analyte itself. In other embodiments, an analyte can be chemically converted into another form in order to make the process of detection easier. By way of example, an enzyme can be used to convert an analyte into another compound that is easier to detect. For example, the hydrolysis of creatinine into ammonia and N-methyl hydantoin can be catalyzed by creatinine deiminase and the resulting ammonia can be detected by a chemical sensor.

In some embodiments, chemical sensors herein can include at least two functional elements: a receptor and a transducer. It will be appreciated that other elements can also be included. The receptor part of a chemical sensor can transform chemical information into a form of energy or signal that can be measured by the transducer. The transducer can transform and/or convey the energy or signal carrying the chemical information so as to provide a useful analytical signal.

Chemical sensors can include optical devices that utilize changes of optical phenomena or properties, which are the result of an interaction of the analyte with the receptor part of the sensor. Such optical properties can include: absorbance, caused by the absorptivity of the analyte itself or by a reaction with some suitable indicator; reflectance, using a bodily component, tissue, or fluid, or using an immobilized indicator; luminescence, based on the measurement of the intensity of light emitted by a chemical reaction in the receptor system; fluorescence, measured as the positive emission effect caused by irradiation or selective quenching of fluorescence; refractive index, measured as the result of a change in solution composition, in some cases including surface plasmon resonance effects; optothermal effects, based on a measurement of the thermal effect caused by light absorption; light scattering; or the like. In some embodiments, optical chemical sensors can include an optode.

Chemical sensors can also include electrochemical devices that transform the effect of the electrochemical interaction between an analyte and an electrode into a useful signal. Such sensors can include voltammetric sensors, including amperometric devices. Also included are sensors based on chemically inert electrodes, chemically active electrodes and modified electrodes. Also included are sensors with and without (galvanic sensors) a current source. Sensors can also include potentiometric sensors, in which the potential of the indicator electrode (ion-selective electrode, redox electrode, metal oxide electrode, or the like) is measured against a reference electrode. Sensors can include chemically sensitized field effect transistors (CHEMFET) in which the effect of the interaction between the analyte and the active coating is transformed into a change of the source-drain current. Sensors can include potentiometric solid electrolyte gas sensors.

Chemical sensors can also include electrical devices based on measurements, where no electrochemical processes take place, but the signal arises from the change of electrical properties caused by interaction with the analyte. Such sensors can include metal oxide semiconductor sensors based on reversible redox processes of analyte gas components, organic semiconductor sensors, based on the formation of charge transfer complexes, which modify the charge carrier density, electrolytic conductivity sensors, and electric permittivity sensors.

Chemical sensors can also include mass sensitive devices that transform the mass change at a specially modified surface into a change of a property of the support material. The mass change can be caused by accumulation of the analyte. Such sensors can include piezoelectric devices based on the measurement the frequency change of the quartz oscillator plate caused by adsorption of a mass of the analyte at the oscillator and surface acoustic wave devices that depend on the modification of the propagation velocity of a generated acoustical wave affected by the deposition of a definite mass of the analyte.

Chemical sensors can also include magnetic devices based on the change of paramagnetic properties of a gas being analyzed. Chemical sensors can also include thermometric devices based on the measurement of the heat effects of a specific chemical reaction or adsorption that involves the analyte.

In one example of the operation of an optical chemical sensor, analytes of interest from the in vivo environment can diffuse into a chemical sensing element causing a detectable change in the optical properties of the chemical sensing element. Light can be generated by an optical excitation device or emitter, such as an LED or similar device, and can pass through the optical window and into the chemical sensing element. Light can then either be preferentially reflected from or re-emitted by the chemical sensing element proportionally to the sensed analyte and pass back through the optical window before being received by a light detection device or receiver, such as a charge-coupled device (CCD), a photodiode, a junction field effect transistor (JFET) type optical sensor, of complementary metal-oxide semiconductor (CMOS) type optical sensor. Various aspects of exemplary chemical sensors are described in greater detail in U.S. Pat. No. 7,809,441, the content of which is herein incorporated by reference in its entirety.

In another example of the operation of an optical chemical sensor, the optical properties of a tissue or fluid in the body can be directly analyzed. By way of example, light can be generated by an optical excitation device that can be delivered to a component, tissue, or fluid in the body and a light detection device can be used to sense an optical property of the light that has interfaced with the component, tissue, or fluid.

Physiological Analytes Measured

Examples of physiological analytes that can be measured in accordance with embodiments herein can include physiological analytes such as, but not limited to, electrolytes, proteins, sugars, hormones, peptides, amino acids, metabolites, and the like. In some embodiments, the electrolytes that can be measured can include potassium, calcium, sodium, magnesium, hydrogen phosphate, chloride, bicarbonate, and the like.

Sensors herein can be directed at a specific physiological analyte or a plurality of different physiological analytes. In an embodiment, the physiological analyte sensed can be one or more physiological analytes relevant to cardiac health. In an embodiment, the physiological analyte sensed can be one or more analytes indicative of renal health. In an embodiment, the physiological analyte sensed can be one or more analytes indicative of pulmonary health. In an embodiment, the physiological analyte sensed can be one or more analytes indicative of neuronal health. The physiological analyte sensed can be an ion or a non-ion. The physiological analyte sensed can be a cation or an anion.

Specific examples of physiological analytes that can be sensed include acetic acid (acetate), aconitic acid (aconitate), ammonium, hemoglobin, blood urea nitrogen (BUN), B-type natriuretic peptide (BNP), bromate, c reactive protein, calcium, carbon dioxide, cardiac specific troponin, chloride, choline, citric acid (citrate), cortisol, copper, creatinine, creatinine kinase, epinephrine, fluoride, formic acid (formate), glucose, hydronium ion, isocitrate, lactic acid (lactate), lithium, magnesium, maleic acid (maleate), malonic acid (malonate), myoglobin, nitrate, nitric-oxide, norepinephrine, oxalic acid (oxalate), oxygen, phosphate, phthalate, potassium, pyruvic acid (pyruvate), selenite, sodium, sulfate, urea, uric acid, and zinc. Inorganic cations sensed by this method include but not limited to hydronium ion, lithium ion, sodium ion, potassium ion, magnesium ion, calcium ion, silver ion, zinc ion, mercury ion, lead ion and ammonium ion. Inorganic anions sensed by this method include but not limited to carbonate anion, nitrate anion, sulfite anion, chloride anion and iodide anion. Organic cations sensed by this method include but are not limited to norephedrine, ephedrine, amphetamine, procaine, prilocaine, lidocaine, bupivacaine, lignocaine, creatinine and protamine. Organic anions sensed by this method include but not limited to salicylate, phthalate, maleate, and heparin. Neutral analytes sensed by this method include but not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

In some embodiments, the physiological analytes can specifically include one or more of sodium ion, magnesium ion, chloride ion, calcium ion, carbonate ion, phosphate ion, sulfate ion, insulin, aldosterone, troponin, glucose, creatinine, and BNP.

In some embodiments, the analytes can specifically include one or more of partial pressure of oxygen ($PaO_2$), partial pressure of carbon dioxide ($PaCO_2$) and oxygen saturation ($O_2Sat$).

Sensor Blending Approaches

Various approaches to blending sensor values can be used. In some embodiments, in order to accommodate varying response times, gain and offset characteristics of individual sensors, values from individual sensors can be blended according to the following equation:

$$S_b(t) = AS_1(t) + BS_2(t) + f(S_1, S_2, t)$$

wherein $S_b$, $S_1$, $S_2$ are blended sensor, $1^{st}$ sensor and $2^{nd}$ sensor respectively; $f(S_1, S_2, t)$ is a function the $1^{st}$ sensor, the $2^{nd}$ sensor and time; and A and B are constant gain coefficients.

In a specific embodiment, values from individual sensors can be blended according to the following equation:

$$S_b(t) = S_2(t) + f(S_1, t)$$

wherein $f(S_1, t)$ is a highpass filtered version of $S_1$; and A=0, B=1.

Figure 2:
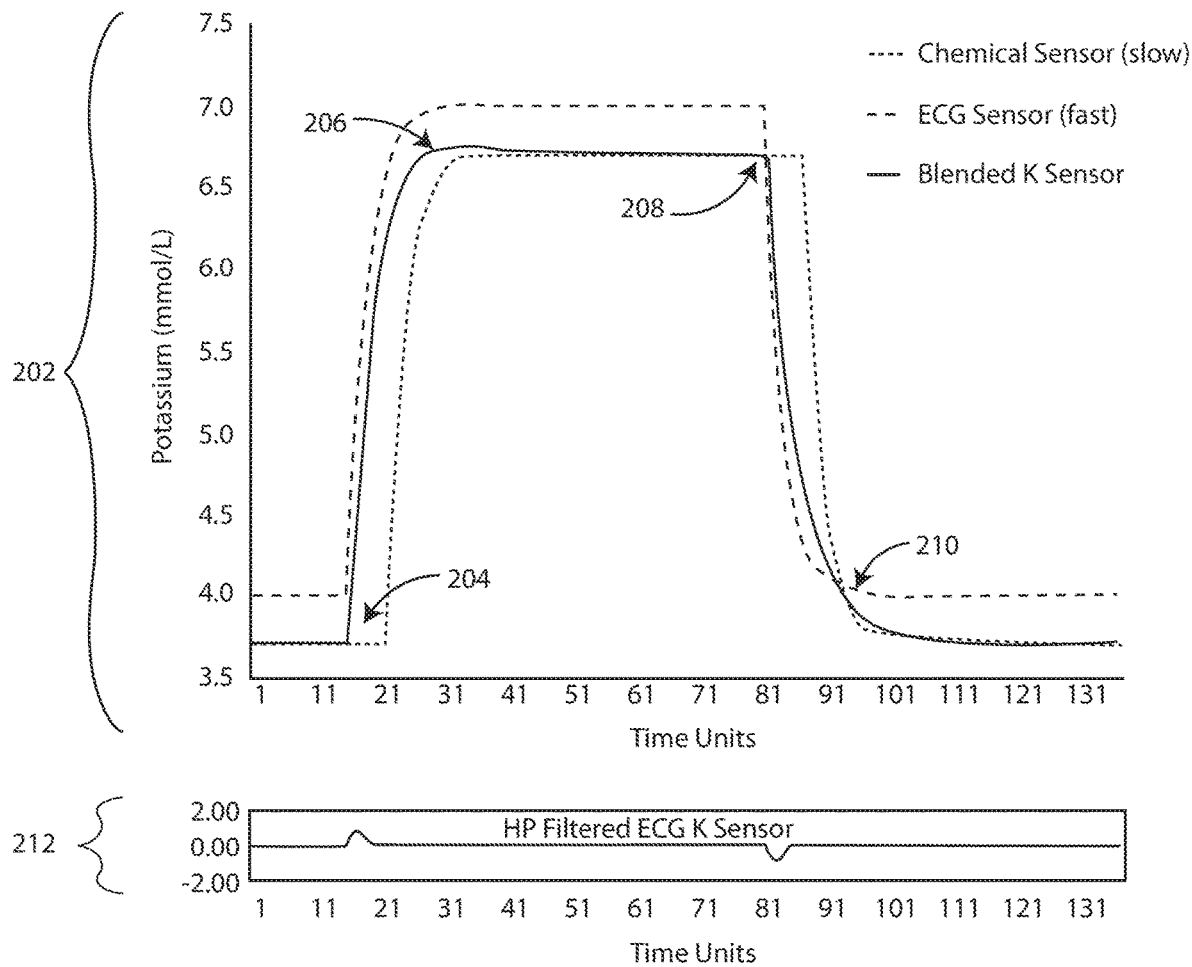
FIG. 2 is a graph of data from a first sensor (a fast response sensor such as an ECG sensor), data from a second sensor (a high accuracy sensor such as a chemical sensor)

Referring now to FIG. 2, a graph is shown of data from a first sensor (a fast response sensor such as an ECG sensor), data from a second sensor (a high accuracy sensor such as a chemical sensor); and blended values for an analyte resulting from blending the data from the first sensor and the data from the second sensor. In this example, it can be seen that the blended value rejects ECG potassium sensor offsets (e.g., relies upon the chemical sensor values at periods without rapid change), but follows the ECG potassium sensor values during rapid changes. In this manner, the blended value exhibits greater accuracy than would be possible by using only the ECG data or the chemical sensor data in isolation.

Further Embodiments of Systems and Methods

In an embodiment herein, a medical system is included that has a first sensor configured to produce a first value for an analyte and a second sensor different than the first sensor, the second sensor configured to produce a second value for the analyte. The system also includes a controller configured to receive the first and second values.

In accordance with various embodiments, including methods herein, the controller creates a blended analyte value from the first value and second value. For example, in some embodiments, the controller creates a blended analyte value by using the first value to normalize the second value or by using the second value to normalize the first value. In some embodiments, the blended analyte value is created using a method that reduces at least one of sensor offset errors, sensor gain errors and sensor latency.

In some embodiments, at least one of the first sensor and the second sensor is implantable. In some embodiments, the first sensor and the second sensor are integrated into the same piece of hardware. In some embodiments, at least one of the first sensor and the second sensor is an optical sensor. In some embodiments, the optical sensor is a sensor array. In some embodiments, at least one of the first sensor and the second sensor is a chemical sensor. In some embodiments, the analyte sensor measures one or more of an electrolyte, a protein, a sugar, a hormone, a peptide, an amino acid and a metabolic product. In some embodiments the electrolyte is at least one of potassium, calcium, sodium, magnesium, hydrogen phosphate, chloride and bicarbonate. In some embodiments the analyte sensor measures pH. In some embodiments, at least one of the first sensor and the second sensor is an ECG sensor. In some embodiments the first sensor is faster reacting than the second sensor (e.g., has a faster response time). In some embodiments, the first sensor is an ECG sensor and the second sensor is a chemical sensor.

In some embodiments, a medical system is included have a first sensor, a second sensor, and a controller. In some embodiments, the controller triggers a measurement change of the second sensor based on the first value for the analyte. In some embodiments, the measurement change can be selected from the group consisting of sampling frequency, measurement schedule, measurement intensity, and turning the sensor on or off. In various embodiments, the first sensor has a faster response time than the second sensor. In various embodiments, data from the first sensor is used for trend analysis of data from the second sensor. In various embodiments, data from the second sensor is used for trend analysis of data from the first sensor.

Devices

Sensors and other components herein can be a part of many different specific devices including implantable devices, external devices, wearable devices, holdable devices, and the like. Specific devices can include, but are not limited to, cardiac rhythm management devices such as pacemakers, implantable cardioverter defibrillators (ICDs), cardiac resynchronization therapy (CRT) devices, implantable monitors, neurostimulation devices, and the like. Sensors and other components herein can all be a part of the same device or can be distributed across separate devices that can be in communication with one another directly or indirectly.

Referring now to FIG. 3, a schematic view is shown of a medical device system 300 in accordance with the embodiments. In some embodiments, medical device system 300 can include an implantable medical device 302, as shown in FIG. 3. In other embodiments, at least a portion of the medical device system can be implantable. In some embodiments, the implantable medical device 302 can include an implantable loop recorder, implantable monitor device, or the like. In some embodiments, implantable medical device 302 can be implanted within the body of a patient 304. Various implant sites can be used including areas on the limbs, the upper torso, the abdominal area, and the like. In some embodiments, the medical device system can include one or more additional medical devices that are communicatively coupled to one another.

Referring now to FIG. 4, a schematic cross-sectional view of the implantable medical device 302 is shown in accordance with various embodiments herein. The implantable device 302 includes a housing 402. The housing 402 can include various materials such as metals, polymers, ceramics, and the like. In some embodiments, the housing 402 can be a single integrated unit. In other embodiments, the housing 402 can include a main segment 404 along with appendage segments 406 and 408. In one embodiment, the housing 402, or one or more portions thereof, can be formed of titanium. In some embodiments, one or more segments of the housing 402 can be hermetically sealed. In some embodiments, the main segment 404 can be formed of a metal and the appendage segments 406 and 408 can be formed from a polymeric material.

The housing 402 defines an interior volume 410 that in some embodiments is hermetically sealed off from the area 412 outside of the implantable medical device. The implantable medical device 302 can include circuitry 450. The circuitry 450 can include various components, including, but not limited to a controller 451, a sensor 452 (e.g., an accelerometer, a gyroscope, a microphone, a bio-impedance sensor), a microprocessor 453, therapy unit circuitry 454, recorder circuitry 455, and sensor interface circuitry 456. Other examples of components suitable for use in the medical device systems embodied herein can include telemetry circuitry, memory circuitry (e.g., such as random access memory (RAM) and/or read only memory (ROM)), power supply circuitry (which can include, but not be limited to, one or more batteries, a capacitor, a power interface circuit, etc.), normalization circuitry, control circuitry, electrical field sensor and stimulation circuitry, display circuitry, and the like.

In some embodiments, one or more components can be integrated into the implantable medical device and in other embodiments one or more components can be separate. In some embodiments recorder circuitry can record the data produced by the chemical sensor and/or the sensor 452 and record time stamps regarding the same. In some embodiments, the circuitry can be hardwired to execute various functions while in other embodiments, the circuitry can be implemented as instructions executing on a controller, a microprocessor, other computation device, application specific integrated circuit (ASIC), or the like.

Implantable medical device 302 can include a sensor 452. In some embodiments, sensor 452 can be a multi-axis accelerometer, such as a 3-axis accelerometer or a 6-axis accelerometer. Sensor 452 can be configured to measure position data of a patient. In some embodiments, sensor 452 can be configured to measure a preliminary position of a patient at a given time point. In some embodiments, sensor 452 can be configured to measure a final position of a patient at a given time point. In some embodiments, sensor 452 can be configured to measure multiple position variations of a patient over a given time period.

In some embodiments, the implantable medical device 302 can include a chemical sensor 420. However, in other embodiments, the chemical sensor may be external such as with in vitro testing. In the embodiment shown in FIG. 4, the chemical sensor is an optical chemical sensor. However, in other embodiments the chemical sensor can be a potentiometric chemical sensor. The chemical sensor 420 can specifically include at least one chemical sensing element 422, an optical window 424, and an electro-optical module 428. The electro-optical module 428 can be in electrical communication with the circuitry 450 within the interior volume 410. In some embodiments, the control circuitry 450 is configured to selectively activate the chemical sensor 420. The chemical sensor 420 can be configured to be chronically implanted or it can be configured to be temporarily implanted. In some embodiments, the chemical sensor 420 can be configured to measure a cellular interstitial component, a blood component, or a breath component, or any analytes thereof. In some embodiments the blood component can include blood constituents or analytes thereof, such as red blood cells; white blood cells including at least neutrophils, eosinophils, and basophils; platelets; hemoglobin; and the like.

The chemical sensor 420 can include an electro-optical module 428 coupled to the optical window 424. The electro-optical module 428 can specifically include one or more optical excitation assemblies. Each optical excitation assembly can include various light sources such as light-emitting diodes (LEDs), vertical-cavity surface-emitting lasers (VC-SELs), electroluminescent (EL) devices or the like. The electro-optical module 428 can also include one or more optical detection assemblies. Each optical detection assembly can include one or more photodiodes, avalanche photodiodes, a photodiode array, a photo transistor, a multi-element photo sensor, a complementary metal oxide semiconductor (CMOS) photo sensor, or the like.

The chemical sensing element 422 can be disposed on the optical window 424. The chemical sensing element 422 can be configured to detect a physiological analyte by exhibiting an optically detectable response to the physiological analyte. Specific examples of physiological analytes are discussed in greater detail below. In operation, physiological analytes of interest from the in vivo environment can diffuse into the chemical sensing element 422 causing a detectable change in the optical properties of the chemical sensing element 422. Light can be generated by the electro-optical module 428 and can pass through the optical window 424 and into the chemical sensing element 422. Light can then either be preferentially reflected from or re-emitted by the chemical sensing element 422 proportional to the sensed physiological analyte, and pass back through the optical window 424 before being received by the electro-optical module 428. Data regarding the specific physiological analyte of interest can be recorded by recorder circuitry 455 for use at a later time.

In some embodiments the chemical sensing element 422 can be located in a fluid such as blood, interstitial fluid, urine, lymph or chyle, and the sensing element 422 can sense physiological analytes in a fluid. In other embodiments, the chemical sensing element 422 can be located in a solid tissue such as cardiac or skeletal muscle, fat, bone, bone marrow, organ tissues (e.g. kidney, liver, brain, lung, etc.), and the sensing element 422 can sense physiological analytes in a solid tissue.

The implantable medical device 302 can include a controller 451. In some embodiments, the controller 451 can be configured to execute one or more operations described herein. The implantable medical device 302 can include additional components, for example, a therapy unit 454. The therapy unit 454 can be configured to deliver a therapy to a patient and/or control or influence the delivery of a therapy provided by another device. In some embodiments, the therapy unit can be configured to provide optimum therapy to a patient depending on if they are in a recumbent, standing or sitting position. Examples of therapies include, but are not limited to pacing schemes such as rate-adaptive pacing, cardiac-resynchronization therapy (CRT), delivery of a neurostimulation therapy, administration of therapeutic agents, and the like. In some embodiments, the therapy unit 454 can be a pharmaceutical therapy unit. In some embodiments, the therapy unit 454 can include both an electrical therapy unit and a pharmaceutical therapy unit. In some embodiments, the therapy unit 454 can be directed by the controller 451 to deliver a therapy to a patient.

An exemplary electrical stimulation therapy unit can include an electrical field sensor that is configured to generate a signal corresponding to cardiac electric fields. The electrical field sensor can include a first electrode 482 and a second electrode 484. In some embodiments, the housing 402 itself can serve as an electrode. The electrodes can be in communication with the electrical field sensor. The electrical field sensor can include a circuit in order to measure the electrical potential difference (voltage) between the first electrode 482 and the second electrode 484. The implantable medical device 302 can also include an antenna 480, to allow for unidirectional or bidirectional wireless data communication within the medical device system 300.

In an embodiment first a current (Ii) is passed from electrode 482 to electrode 484 through the tissue surrounding implantable medical device 302. The voltage between electrode 482 and electrode 484 (Vi) is measured and the bio-impedance of the tissue surrounding implantable medical device 302 is determined by dividing Vi by Ii. In some embodiments the bio-impedance is used to determine a respiratory parameter such as respiratory rate or tidal volume. In some embodiments the bio-impedance is used to determine a constituent of the tissue, such as the fluid content.

Elements of some embodiments of a medical device system are shown in FIG. 5 in accordance with the embodiments herein. However, it will be appreciated that some embodiments can include additional elements beyond those shown in FIG. 5. In addition, some embodiments may lack some elements shown in FIG. 5. The medical device system, as embodied herein, can gather information through one or more sensing channels 520, 530, 540. A controller 510 can communicate with a memory 512 via a bidirectional data bus. The memory 512 can include read only memory (ROM) or random access memory (RAM) for program storage and RAM for data storage.

In some embodiments, a medical device can include one or more electric field sensors 522 (i.e., electrodes) and an electric field sensor channel interface 520 that can communicate with a port of controller 510. The medical device can also include another type of sensor 532 and a sensor channel interface 530 for the same that can communicate with a port of controller 510. The medical device can also include one or more chemical sensors 542 and a chemical sensor channel interface 540 that can communicate with a port of controller 510. The channel interfaces 520, 530 and 540 can include various components such as analog-to-digital converters for digitizing signal inputs, sensing amplifiers, registers that can be written to by the control circuitry in order to adjust the gain and threshold values for the sensing amplifiers, and the like. A telemetry interface 514 is also provided for communicating with external devices such as a programmer, a home-based unit, and/or a mobile unit (e.g. a cellular phone, laptop computer, etc.).

In some embodiments, the medical device can also include additional sensors, such as posture sensors, activity sensors, or respiration sensors integral to the medical device. In some embodiments, the medical device can also include additional sensors that are separate from medical device. In various embodiments one or more of the posture sensors, activity sensors, or respiration sensors can be within another implanted medical device communicatively coupled to the medical device via telemetry interface 514. In various embodiments one or more of the additional posture sensors, activity sensors, or respiration sensors can be external to the body and are coupled to medical device via telemetry interface 514.

Referring now to FIG. 6, a schematic view is shown of a medical device system 600 in accordance with the embodiments herein. The medical device system 600 can include an implantable medical device 602 and one or more stimulation leads 640, 646, and 654. In various embodiments, the implantable medical device 602 can include a therapy unit such as a cardiac rhythm management device, including a pacemaker, a cardiac resynchronization therapy (CRT) device, a remodeling control therapy (RCT) device, a cardioverter/defibrillator, or a device providing two or more of these therapies. In some embodiments, the implantable medical device 602 can be, or also include, a neurological stimulation device. In some embodiments, the implantable medical device 602 can be, or also include, a pharmaceutical delivery device.

The implantable medical device 602 can include a pulse generator housing 604 and a header 608. The term "pulse generator housing" as used herein shall refer to the part or parts of an implanted medical device, such as a cardiac rhythm management device, neurological therapy device, or pharmaceutical delivery device containing the power source and circuitry for delivering pacing therapy, electrical stimulation, shock therapy, and/or pharmaceutical therapy. Together, the pulse generator housing 604, the contents therein, and the header assembly 608 can be referred to as a pulse generator. It will be appreciated that embodiments herein can also be used in conjunction with implantable medical devices that may lack pulse generators such as monitoring devices and pharmaceutical delivery devices.

In FIG. 6, the proximal ends of the stimulation leads 640, 646, and 654 are disposed within the header assembly 608. The stimulation leads 640, 646, and 654 can pass to the heart 652 transvenously. In this view, stimulation lead 640 passes into the coronary venous system, stimulation lead 646 passes into the right atrium, and stimulation lead 654 passes into the right ventricle. However, it will be appreciated that stimulation leads can be disposed in various places within or around the heart. Stimulation lead 640 includes a tip electrode 642 and a ring electrode 644. Stimulation leads 646 and 654 also include tip electrodes 650 and 658 and ring electrodes 648 and 656, respectively. It will be appreciated that stimulation leads can include different numbers of electrodes. For example, in some embodiments, a stimulation lead may only include a single electrode and in some embodiments a stimulation lead may include more than two electrodes. Depending on the configuration, the stimulation leads can provide electrical and/or optical communication between the distal ends of the stimulation leads and the pulse generator. In operation, the pulse generator may generate pacing pulses or therapeutic shocks which are delivered to the heart 652 via the electrodes of the stimulation leads. In many embodiments, the stimulation leads include a material that is electrically conductive in order to deliver the pacing pulses or therapeutic shocks.

The medical device system 600 can also be configured to sense electrical activity of the heart. By way of example, the medical device system 600 can include an electrical field sensor, such as shown in FIG. 7 as part of control circuitry 751. Specifically, the medical device system 400 can use one or more electrodes, such as the electrodes on the stimulation leads 642, 644, 648, 650, 656, and/or 658, in order to sense electrical activity of the heart, such as a time-varying electrical potential. In some embodiments, the pulse generator housing 604 can serve as an electrode for purposes of sensing electrical activity and/or delivering electrical stimulation.

The medical device system 600 can also include a chemical sensor 606. The chemical sensor 606 (such as described above in reference to FIG. 3) can be configured to measure the concentration of physiological analytes such as those described below.

Referring now to FIG. 7, a schematic cross-sectional view of an implantable medical device 602, as shown in FIG. 6. The implantable medical device 602 includes a pulse generator housing 604 a header assembly 608. The pulse generator housing 604 of the implantable medical device 602 can include various materials such as metals, polymers, ceramics, and the like. In one embodiment, the pulse generator housing 604 is formed of titanium. The header assembly 608 can be coupled to one or more electrical stimulation leads 750. The header assembly 608 can serve to provide fixation of the proximal end of one or more leads and electrically couples the leads to components within the pulse generator housing 604. The header assembly 608 can be formed of various materials including metals, polymers, ceramics, and the like.

The pulse generator housing 604 defines an interior volume 770 that is hermetically sealed off from the volume 772 outside of the device 700. Various electrical conductors 709, 711 can pass from the header assembly 608 through a feed-through structure 705, and into the interior volume 770. As such, the conductors 709, 711 can serve to provide electrical communication between the electrical stimulation lead 750 and control circuitry 751 disposed within the interior volume 770 of the pulse generator housing 604.

Control circuitry 751 can include many of the same features as those presented above in reference to implantable medical device 302, such as, for example a controller 451, a sensor 452, a microprocessor 453, therapy unit circuitry 454, recorder circuitry 455, and sensor interface circuitry 456. In some embodiments, control circuitry 751 can include additional features that are not present in reference to implantable medical device 302. In some embodiments, control circuitry can include fewer features than those presented with respect to implantable medical device 302. The control circuitry 751 can include additional components such memory (such as random access memory (RAM) and/or read only memory (ROM)), a telemetry module, electrical field sensor and stimulation circuitry, a power supply (such as a battery), normalization circuitry, and an optical sensor interface channel, amongst others.

The implantable medical device 602 can also include a chemical sensor 606. In the embodiment shown in FIG. 7, the chemical sensor 606 is a potentiometric chemical sensor. The chemical sensor 606 can specifically include a receptor module 722, and a transducer module 728. The transducer module 728 can be in electrical communication with the control circuitry 751 within the interior volume 770, and in some embodiments, the control circuitry 551 can be configured to selectively activate the chemical sensor (such as, e.g., using the controller 451). In some embodiments, the chemical sensor 606 can be configured to be chronically implanted. In some embodiments, the chemical sensor 606 can be configured to be temporarily implanted.

The chemical sensor 606 can be configured to detect a physiological analyte by exhibiting an electrical signal response to the physiological analyte. In operation, physiological analytes of interest from the in vivo environment can contact the receptor module 722 causing a detectable change in the electrical properties of the same. The transducer module 728 can then be used to process and/or propagate the signal created by the receptor module 722.

Similar to the implantable medical device 302 shown in FIG. 3, the implantable medical device 602 can also include a sensor 452. Sensor 452 can include a multi-axis accelerometer, such as a 3-axis accelerometer or a 6-axis accelerometer. Sensor 452 can be configured to measure position data of a patient. In some embodiments, sensor 452 can be configured to measure a preliminary position of a patient at a given time point. In some embodiments, accelerometer 452 can be configured to measure a final position of a patient at a given time point. In some embodiments, sensor 452 can be configured to measure multiple position variations of a patient over a given time period.

The implantable medical device 602 can incorporate, for example, an electrical field sensor that is configured to generate a signal corresponding to cardiac electric fields. The electrical field sensor can include a first electrode and a second electrode. The electrodes of the electrical field sensor can be the same electrodes used to provide electrical stimulation (such as referred to with respect to FIG. 6) or can be different electrodes. In some embodiments, one or more electrodes can be mounted on one or more electrical stimulation leads 750. In some embodiments, the pulse generator housing 604 can serve as an electrode. The electrodes can be in communication with the electrical field sensor and stimulation circuitry. The electrical field sensor and stimulation circuitry can be used in order to measure the electrical potential difference (voltage) between the first electrode and the second electrode.

Elements of some embodiments of an implantable medical device 602 are shown in FIG. 8. However, it will be appreciated that some embodiments can include additional elements beyond those shown in FIG. 8. In addition, some embodiments may lack some elements shown in FIG. 8. The implantable medical device 602 can sense cardiac events through one or more sensing channels and outputs pacing pulses to the heart via one or more pacing channels in accordance with a programmed pacing mode. A controller 802 communicates with a memory 807 via a bidirectional data bus. The memory 807 typically comprises read only memory (ROM) or random access memory (RAM) for program storage and RAM for data storage.

The implantable medical device can include atrial sensing and pacing channels comprising at least a first electrode 826, lead 824, sensing amplifier 822, output circuit 823, and an atrial channel interface 820, which can communicate bidirectionally with a port of controller 802. In this embodiment, the device also has ventricular sensing and pacing channels comprising at least a second electrode 816, lead 814, sensing amplifier 812, output circuit 813, and ventricular channel interface 810, which can communicate bidirectionally with a port of controller 802. For each channel, the same lead and electrode are used for both sensing and pacing. The channel interfaces 810 and 820 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers. The implantable medical device can also include a chemical sensor 842 and a chemical sensor channel interface 840, and another type of sensor 852 and an associated channel interface 850. A telemetry interface 844 is also provided for communicating with an external programmer.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like. "Circuitry" can include both hardwired circuitry for execution of particular operations as well as processors that are programmed to execute instructions to provide the same functionality.

All publications and patent applications in this specification are indicative of the level of ordinary skill in the art to which this specification pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein. As such, the embodiments described herein are not intended to be exhaustive or to limit the scope to the precise forms disclosed herein. Rather, the embodiments are chosen and described so that others skilled in the art can appreciate and understand the principles and practices.

The invention claimed is:

1. A medical system comprising
a first sensor configured to produce a first value for an analyte, wherein the analyte is an electrolyte;
a second sensor configured to produce a second value for the analyte, wherein the second sensor is a different type of sensor than the first sensor; and
a controller configured to receive the first and second values;
wherein the controller triggers a measurement change of the second sensor based on the first value for the analyte and;
wherein the first sensor and the second sensor are implantable;
wherein the first sensor has a faster response time than the second sensor;
wherein the first sensor is an implantable electrical ECG sensor; and
wherein the second sensor is an implantable diffusion based optical chemical sensor.

2. The medical system of claim 1, wherein the measurement change is selected from the group consisting of sampling frequency, measurement schedule, measurement intensity, and turning the sensor on or off.

3. The medical system of claim 1, wherein data from the first sensor is used for trend analysis of data from the second sensor.

4. The medical system of claim 1, wherein data from the second sensor is used for trend analysis of data from the first sensor.

5. The medical system of claim 1, wherein the controller creates a blended analyte value from the first value and second value.

6. The medical system of claim 5, wherein the blended analyte value is created using a method that reduces at least one of sensor offset errors, sensor gain errors and sensor latency.

7. The medical system of claim 1, wherein the first sensor is faster reacting than the second sensor.

8. The medical system of claim 1, wherein the faster response time of the first sensor comprises a response time of from 1 second to 5 minutes, and wherein the response time comprises a time until a steady-state level of sensor response is achieved after a change in the intrinsic value being measure.

9. The medical system of claim 1, wherein the chemical sensor is configured to detect an analyte of interest from the in vivo environment that has diffused into the optical chemical sensor and caused a detectable change in the optical properties of the chemical sensor.

10. A medical system comprising
   a first sensor configured to produce a first value for an analyte, wherein the analyte is an electrolyte;
   a second sensor configured to produce a second value for the analyte, wherein the second sensor is a different type of sensor than the first sensor; and
   a controller configured to receive the first and second values;
   wherein the controller triggers a measurement change of the second sensor based on the first value for the analyte;
   wherein the measurement change is selected from the group consisting of sampling frequency, measurement schedule, and measurement intensity; and
   wherein the first sensor is an implantable electrical ECG sensor and the second sensor is an implantable diffusion based optical chemical sensor; and
   wherein the first sensor has a faster response time than the second sensor.

11. The medical system of claim 10, wherein data from the first sensor is used for trend analysis of data from the second sensor.

12. The medical system of claim 10, wherein data from the second sensor is used for trend analysis of data from the first sensor.

13. The medical system of claim 10, wherein the controller creates a blended analyte value from the first value and second value.

14. A medical system comprising
   a first sensor configured to produce a first value for an analyte, wherein the analyte is an electrolyte;
   a second sensor configured to produce a second value for the analyte, wherein the second sensor is a different type of sensor than the first sensor; and
   a controller configured to receive the first and second values;
   wherein the controller triggers a measurement change of the second sensor based on the first value for the analyte; and
   wherein the first sensor is an implantable electrical ECG sensor and the second sensor is an implantable diffusion based optical chemical sensor; and
   wherein the first sensor has a faster response time than the second sensor.

15. The medical system of claim 14, wherein the controller creates a blended analyte value by using the first value to normalize the second value or by using the second value to normalize the first value.

16. The medical system of claim 15, wherein the blended analyte value is created using a method that reduces at least one of sensor offset errors, sensor gain errors and sensor latency as compared with values from the first sensor and second sensor standing alone.

* * * * *